(12) United States Patent
Dykes et al.

(10) Patent No.: US 9,498,312 B2
(45) Date of Patent: Nov. 22, 2016

(54) ORAL HEALTH CARE IMPLEMENT AND SYSTEM WITH PROXIMITY SENSOR

(71) Applicant: Beam Technologies, LLC, Louisville, KY (US)

(72) Inventors: Daniel E. Dykes, Louisville, KY (US); Alex X. Frommeyer, Louisville, KY (US); Alexander D. Curry, Louisville, KY (US)

(73) Assignee: BEAM TECHNOLOGIES, LLC, Louisville, KY (US)

( * ) Notice: Subject to any disclaimer, the term of this patent is extended or adjusted under 35 U.S.C. 154(b) by 961 days.

(21) Appl. No.: 13/624,896

(22) Filed: Sep. 22, 2012

(65) Prior Publication Data

US 2013/0080295 A1    Mar. 28, 2013

Related U.S. Application Data

(60) Provisional application No. 61/538,392, filed on Sep. 23, 2011.

(51) Int. Cl.
  *A61C 17/22*     (2006.01)
(52) U.S. Cl.
  CPC .................................. *A61C 17/221* (2013.01)
(58) Field of Classification Search
  CPC ............................ A61C 17/22; A61C 17/221
  USPC ..................................... 15/22.1, 21.1; 433/27
  See application file for complete search history.

(56) References Cited

U.S. PATENT DOCUMENTS

| | | | |
|---|---|---|---|
| 4,698,869 A * | 10/1987 | Mierau ............... | A46B 15/0002 15/105 |
| 5,353,460 A * | 10/1994 | Bauman .......................... | 15/22.1 |
| 7,845,041 B2 * | 12/2010 | Gatzemeyer et al. ........... | 15/105 |
| 2007/0228734 A1* | 10/2007 | Gerfast ...................... | F03G 7/08 290/1 R |
| 2009/0038639 A1* | 2/2009 | Yetukuri et al. ................... | 134/6 |
| 2009/0148808 A1* | 6/2009 | Alexander ......... | A46B 15/0002 433/29 |
| 2009/0317770 A1* | 12/2009 | Gatzemeyer et al. ........ | 433/215 |

FOREIGN PATENT DOCUMENTS

GB       2258922 A  * 10/1992   ............. A45D 20/30

* cited by examiner

*Primary Examiner* — Laura C Guidotti
(74) *Attorney, Agent, or Firm* — Alexander D. Curry

(57) ABSTRACT

An oral health care implement and system are provided for use during oral health care activities. The oral health care implement has a proximity sensor, most often in the embodiment of a capacitive sensor. The proximity sensor provides usage time and instance measurements in a plurality of proposed formats. The oral health care system has an oral health care implement, a first data transfer medium, and any combination of: a second data transfer medium, a network storage device, and a third data transfer medium. The system provides means for collecting usage measurements and transmitting data into a readable, usable form for the user via an oral health care implement.

12 Claims, 15 Drawing Sheets

401

| | |
|---|---|
| No. of Brushings: | 25 |
| Avg. Brushing Duration: | 2:00 min. |
| Last Brush Duration: | 1:57 min. |
| Last Brush Date: | 1/1/2011 |
| Last Brush Time: | 8:00 am |
| Lifespan Remaining: | 75 % |
| Plaque Rating: | 8.5 |

Alerts:
Biofilm thickness has increased! Consult your dental practiononer.

Updates: No new updates.

FIG. 14

ORAL HEALTH CARE IMPLEMENT AND SYSTEM WITH PROXIMITY SENSOR

CROSS-REFERENCE TO RELATED APPLICATIONS

This application claims priority to U.S. Provisional Application No. 61/538,392 filed on Sep. 23, 2011.

BACKGROUND OF THE INVENTION

This invention relates to oral health care implements and systems, particularly relating to improved toothbrushes utilizing new technologies for the dental field. In particular, the invention relates to the usage-monitoring capabilities of both manual and electric toothbrushes.

The human body, including the oral cavity, possesses the property of being a good capacitor, such that the human body has a detectable capacitance. The capacitance of the human body is significant enough to affect changes in an electrical circuit with capacitance. The capacitance of the human body can affect the overall capacitance of an electrical circuit when introduced via a conductive material.

Dental plaque is a biofilm that forms naturally on teeth between brushing and dental visits. Dental plaque can be a precursor to more severe oral health problems including: dental caries, tooth decay, gingivitis, and chronic periodontitis. The occurrence of dental caries is one of the largest health epidemics in the world and is the most common chronic childhood disease in the United States. Likewise, gingivitis and dental calculus are two of the most common systemic diseases of the body. It is desirable to monitor and diagnose dental plaque early stage as a preventive measure against more serious disease states. The most common preventive measure implemented to control the formation of dental plaque is the toothbrush.

Further still, clinical dental visits with dental practitioners are a method of prevention and detection of dental plaque. Regular dental visits are recommended to occur every six months. Regular toothbrush replacement is recommended to occur every three months according to dental practitioners. The lack of adherence to these recommendations and lack of brushing compliance is often a contributing factor to the development of dental plaque and its associated complications. Regular replacement of toothbrushes is often disregarded by users and cause issues as bristles become deformed and are no longer providing the proper cleaning.

Consequently, dental practitioners are in need of an adequate means to monitor the usage of dental implements between clinical dental visits. Moreover, dental practitioners are in need of an accurate method of determining the usage of a particular dental implement to make recommendations based upon its usage. Usage monitoring of dental implements has long been difficult as the main method of collecting data is by inquiring a particular patient. Consequently, a method for measuring the usage of dental implements is desirable for dental practitioners.

BRIEF SUMMARY OF THE INVENTION

The invention aims to provide an oral health care implement and system with a proximity sensor for the detection and monitoring oral health care implement usage. The implement is most often a toothbrush 10 that has bristles 25 for cleaning. The toothbrush 10 has a proximity sensor 90 that detects when the toothbrush 10 is in proximity to the user's oral cavity. This allows the user to monitor and track the usage of the toothbrush 10 as well as for multiple toothbrushes.

The proximity detection is transmitted to a first data transfer medium 201 where the data is received, stored, and processed. Optionally, the data is then transmitted to either a second data transfer medium 211 or a network storage device 246, where the data is received, transmitted, stored, and processed. Optionally, the data is then further transmitted to a third data transfer medium 221, where the data is received, transmitted, stored, and processed. Accordingly, the data may be displayed in a user-readable format 401 on either the first data transfer medium 201, the second data transfer medium 211, the third data transfer medium 221, or any combination thereof.

Accordingly, several advantages are to provide an oral health care implement, to provide a means for monitoring implement usage and duration, and to provide transmission of proximity detection data to a convenient display medium. Still further advantages will become apparent from a study of the following descriptions and the accompanying drawings.

BRIEF DESCRIPTION OF THE DRAWINGS

FIG. 14 is an example screen shot of a user-readable format according to multiple embodiments and alternatives.

DETAILED DESCRIPTION OF THE INVENTION

Figure 1:
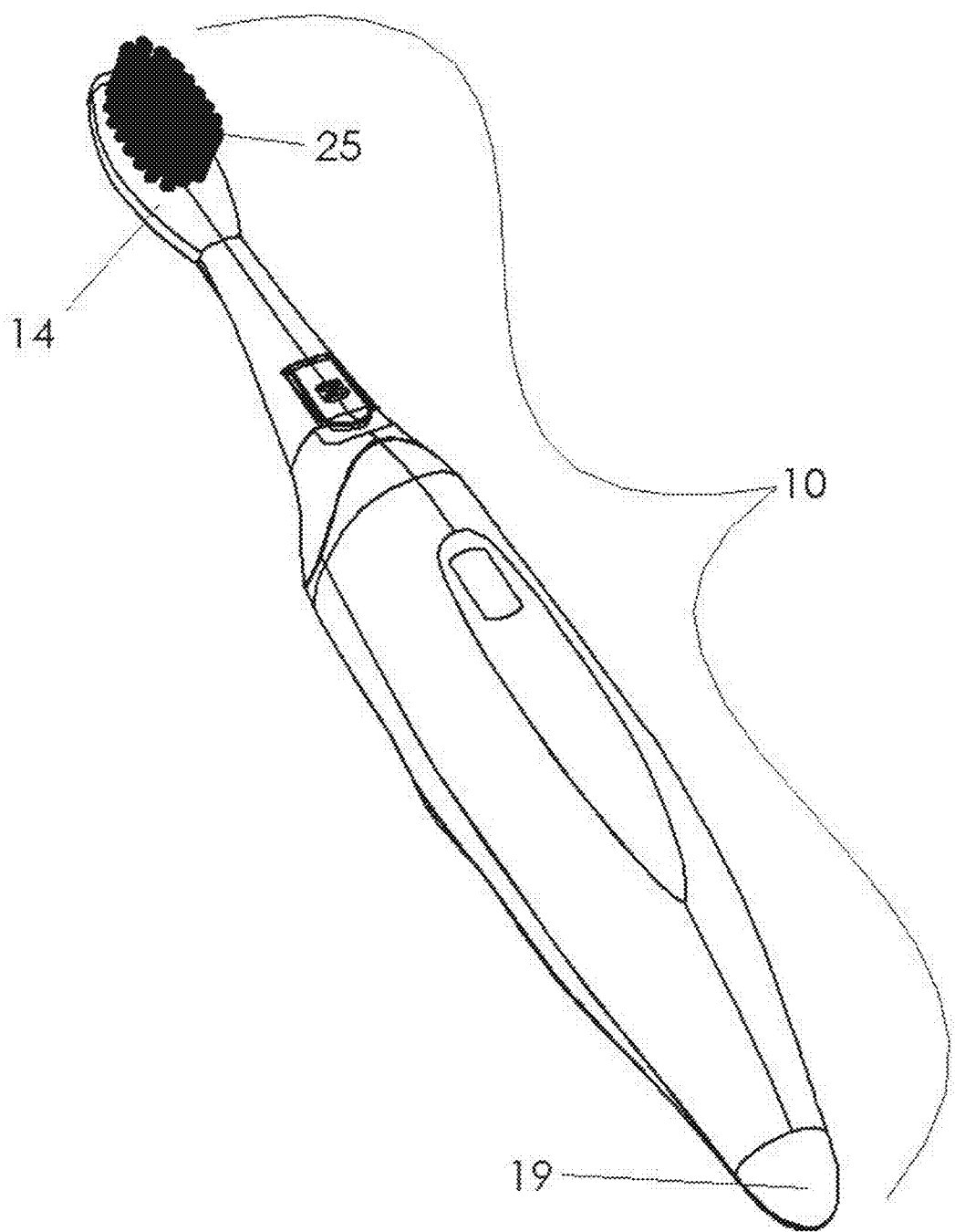
FIG. 1 is a perspective view of a toothbrush with bristles according to multiple embodiments and alternatives.
Figure 2:
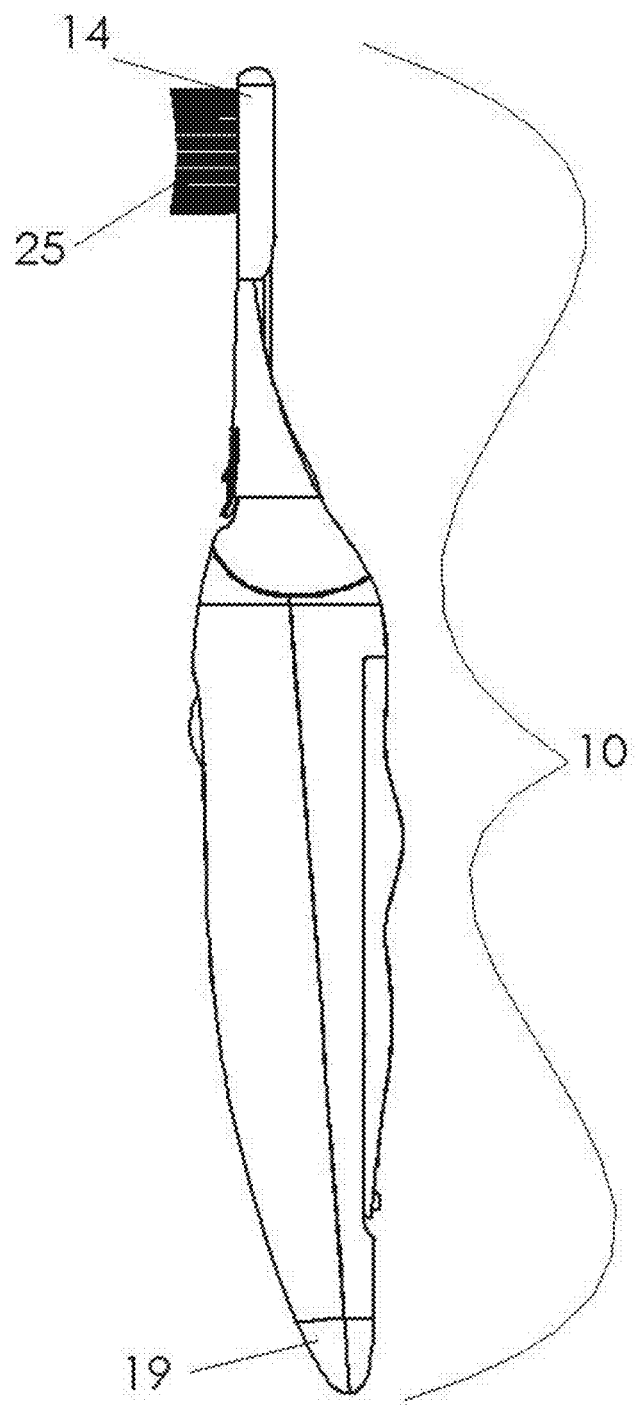
FIG. 2 is a plan view of a toothbrush with bristles according to multiple embodiments and alternatives.
Figures 3A, 3B:
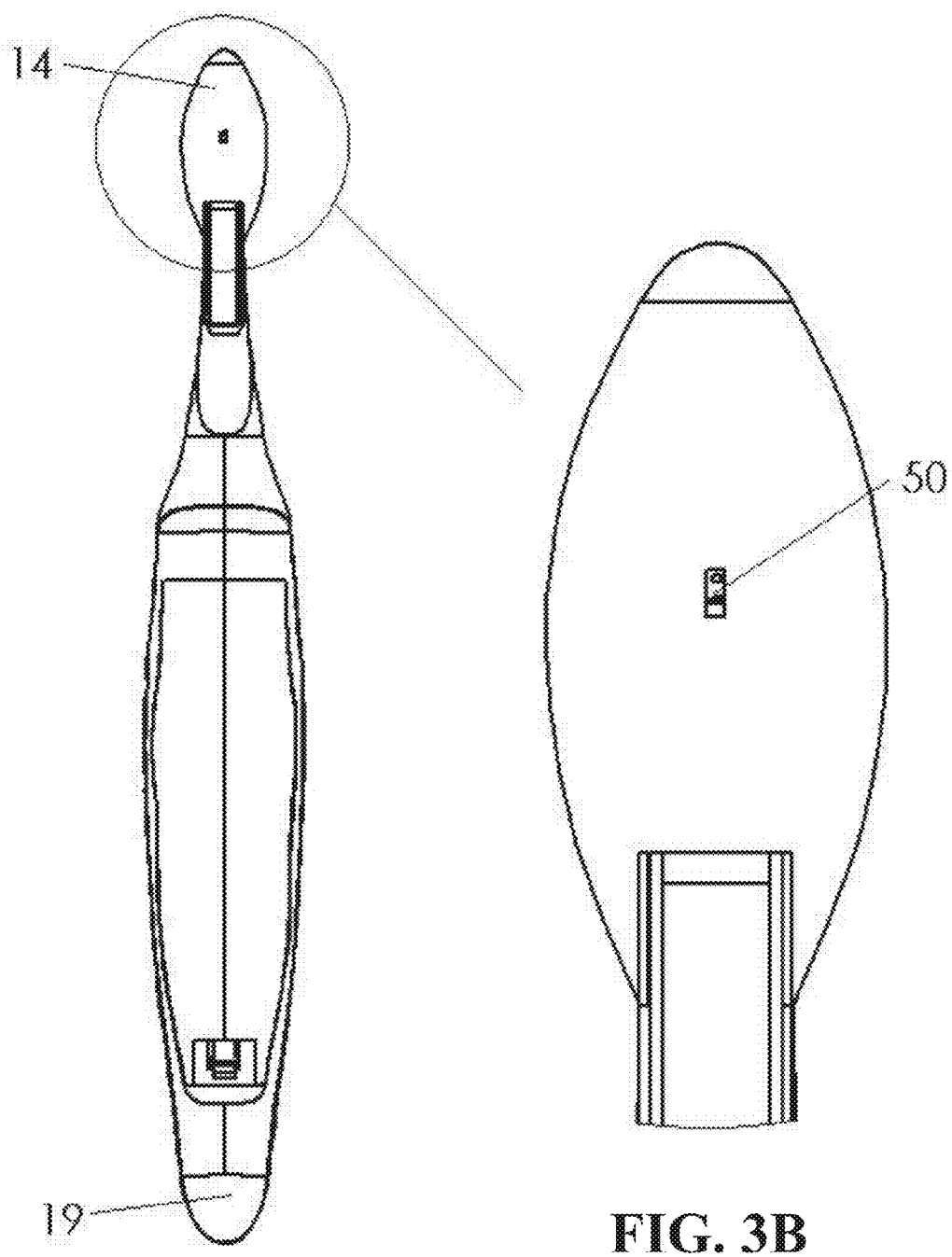
FIG. 3A is a plan view of the back of a toothbrush with a diagnostic ultrasonic sensor according to multiple embodiments and alternatives.
FIG. 3B is a detail view of the back of a toothbrush with a diagnostic ultrasonic sensor according to multiple embodiments and alternatives.
Figure 4A:
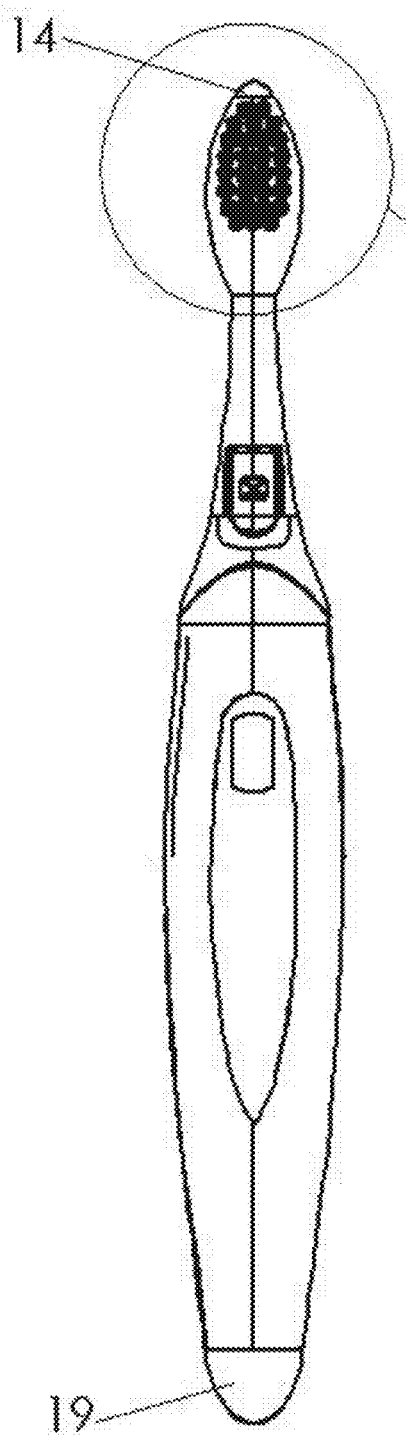
FIG. 4A is a plan view of the front of a toothbrush with a diagnostic ultrasonic sensor according to multiple embodiments and alternatives.
Figure 4B:
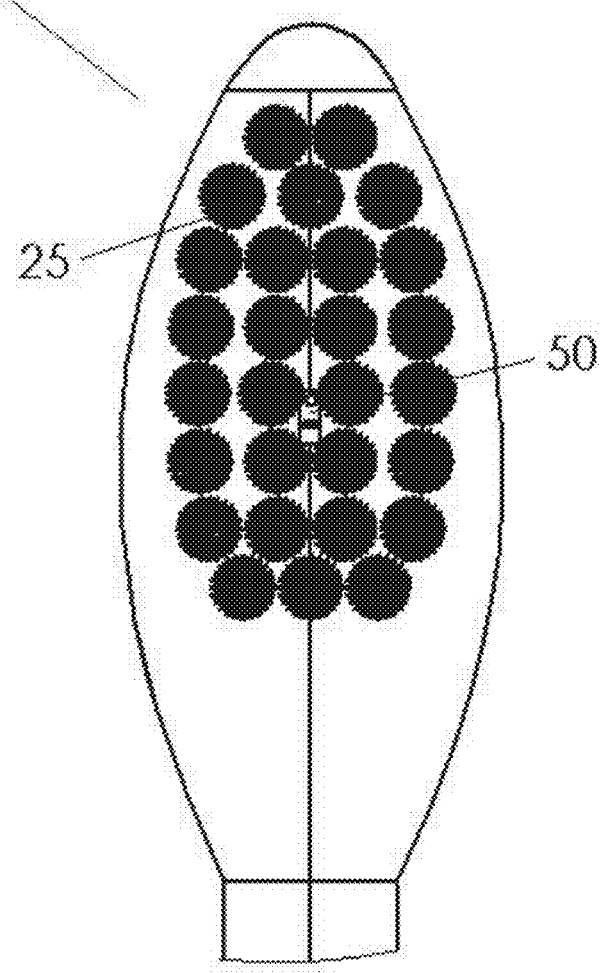
FIG. 4B is a detail view of the front of a toothbrush with a diagnostic ultrasonic sensor according to multiple embodiments and alternatives.
Figure 5:
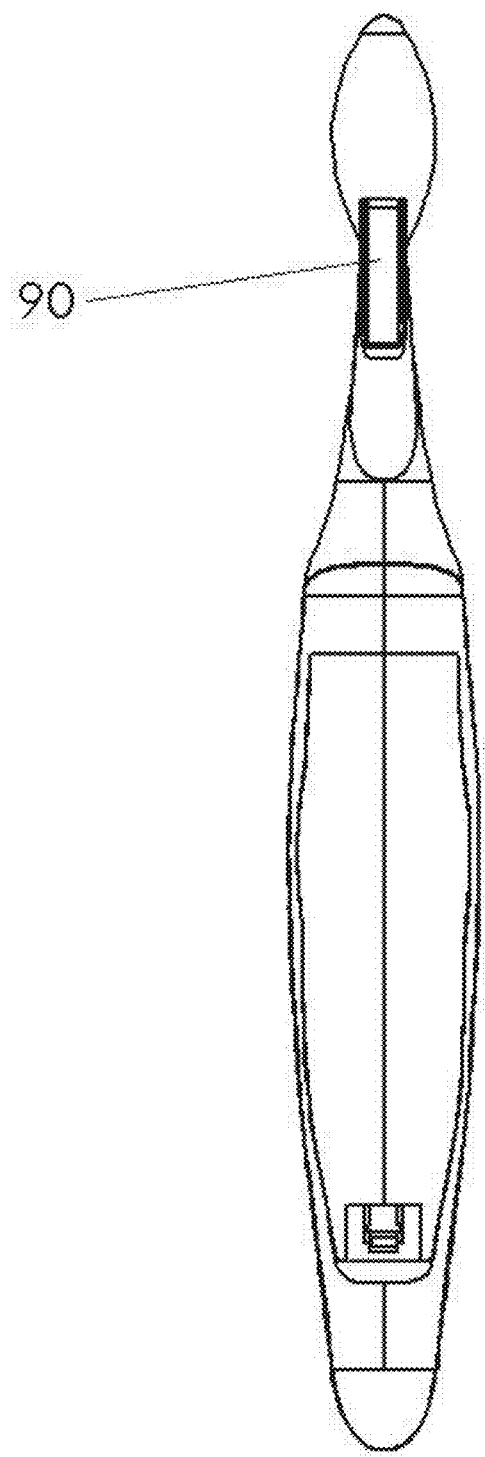
FIG. 5 is a plan view of the back of a toothbrush with a proximity sensor according to multiple embodiments and alternatives.
Figures 6A, 6B, 6C:
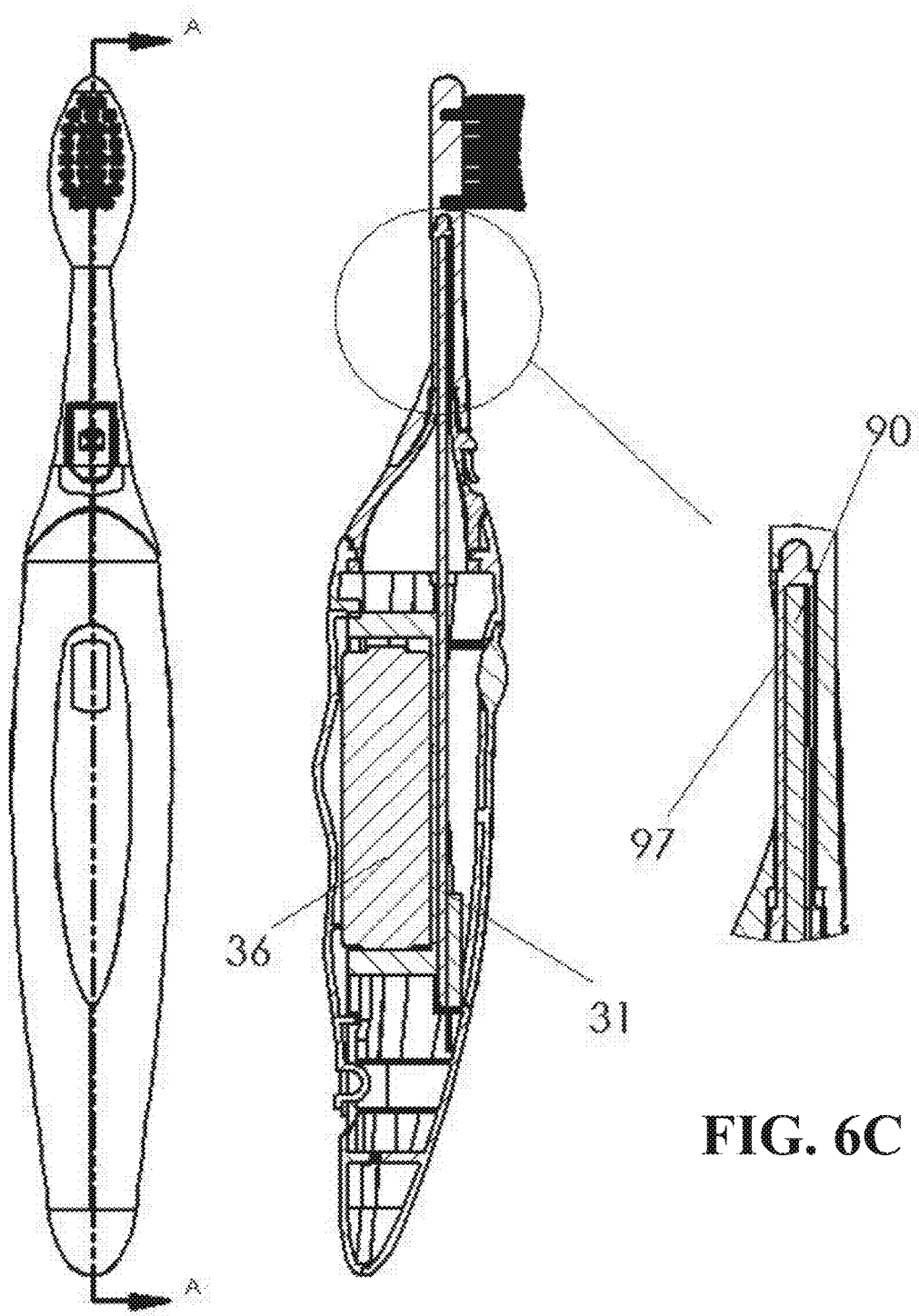
FIG. 6A is a plan view of the front of a toothbrush with a proximity sensor according to multiple embodiments and alternatives.
FIG. 6B is a section view of a toothbrush with a proximity sensor according to multiple embodiments and alternatives.
FIG. 6C is a detail view of a toothbrush with a proximity sensor according to multiple embodiments and alternatives.
Figure 7A:
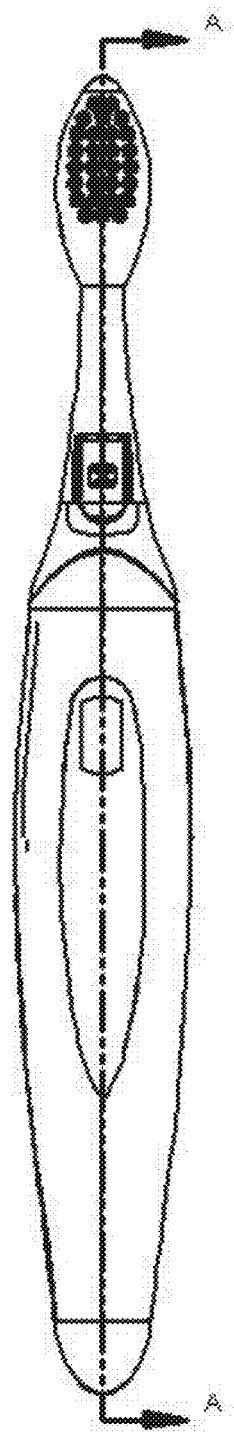
FIG. 7A is a plan view of the front of a toothbrush with a temperature sensor according to multiple embodiments and alternatives.
Figure 7B:
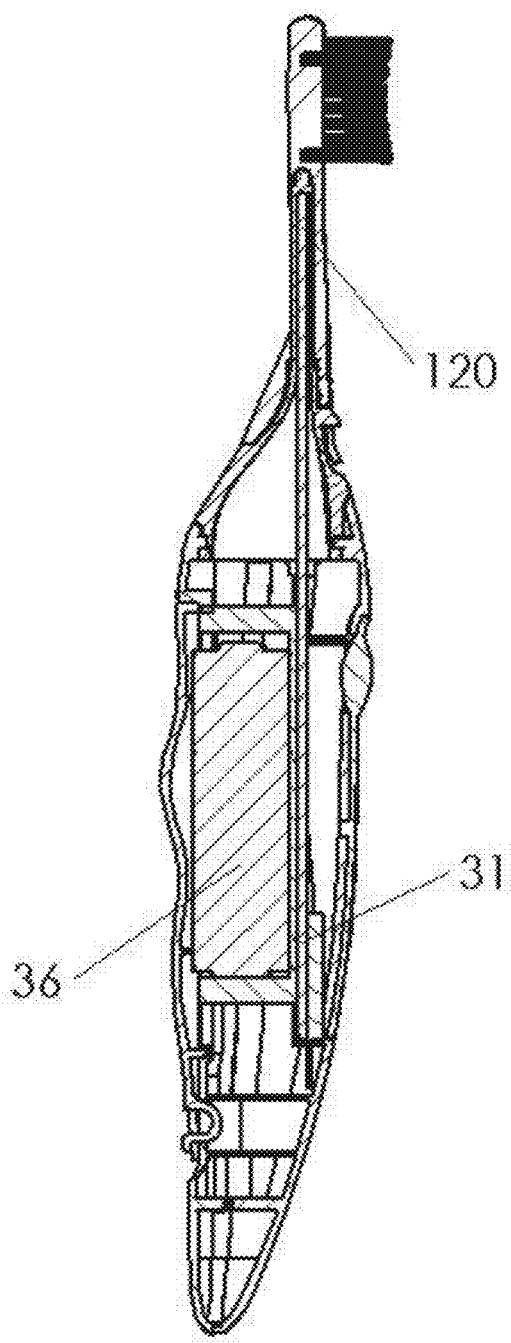
FIG. 7B is a section view of a toothbrush with a temperature sensor according to multiple embodiments and alternatives.
Figure 8:
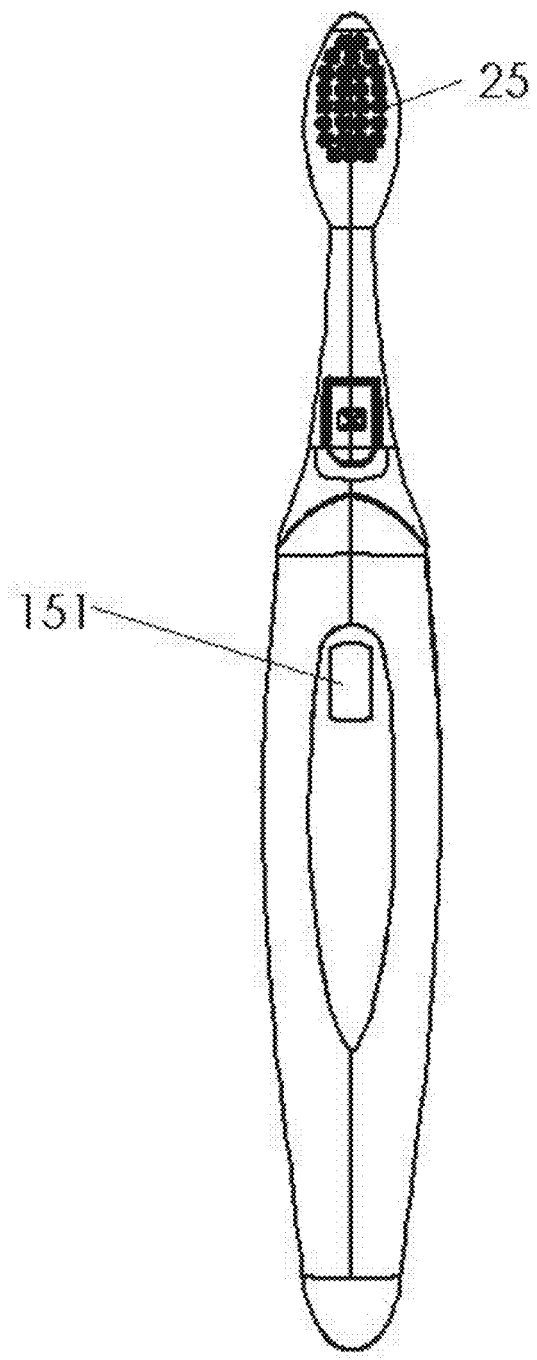
FIG. 8 is a plan view of the front of a toothbrush with an oximetry sensor according to multiple embodiments and alternatives.
Figure 9:
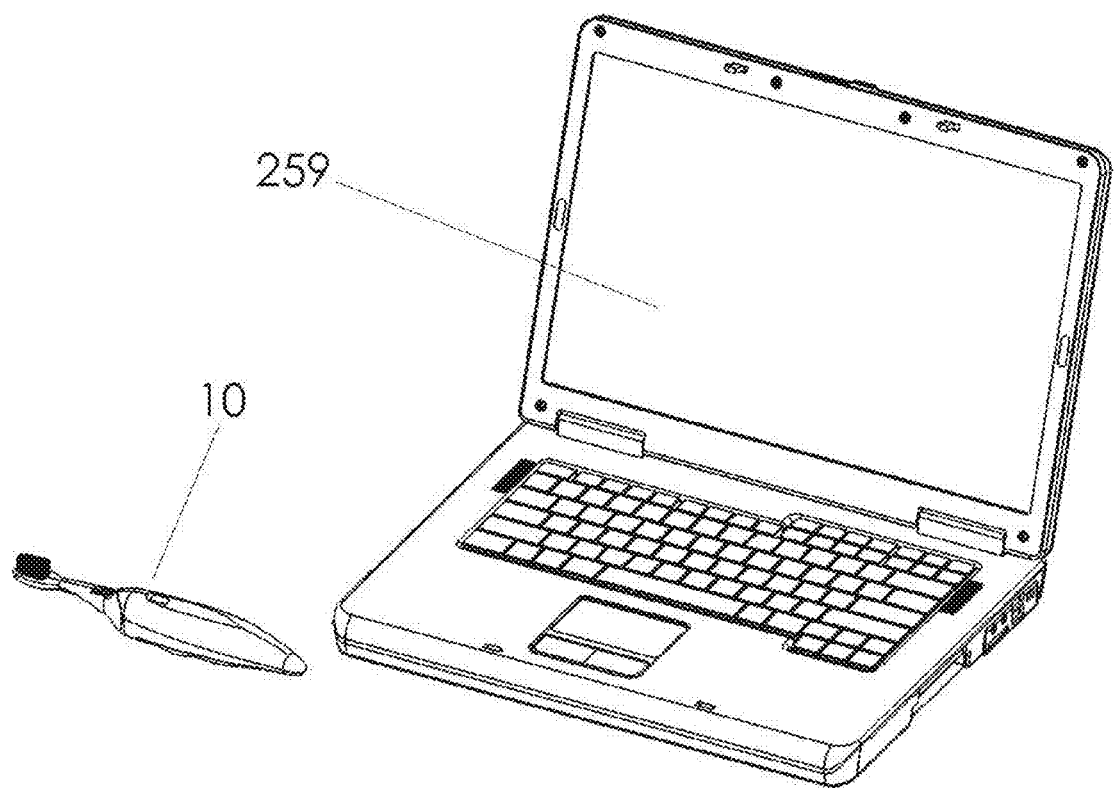
FIG. 9 is a perspective view of a toothbrush and a personal computer system according to multiple embodiments and alternatives.
Figure 10:
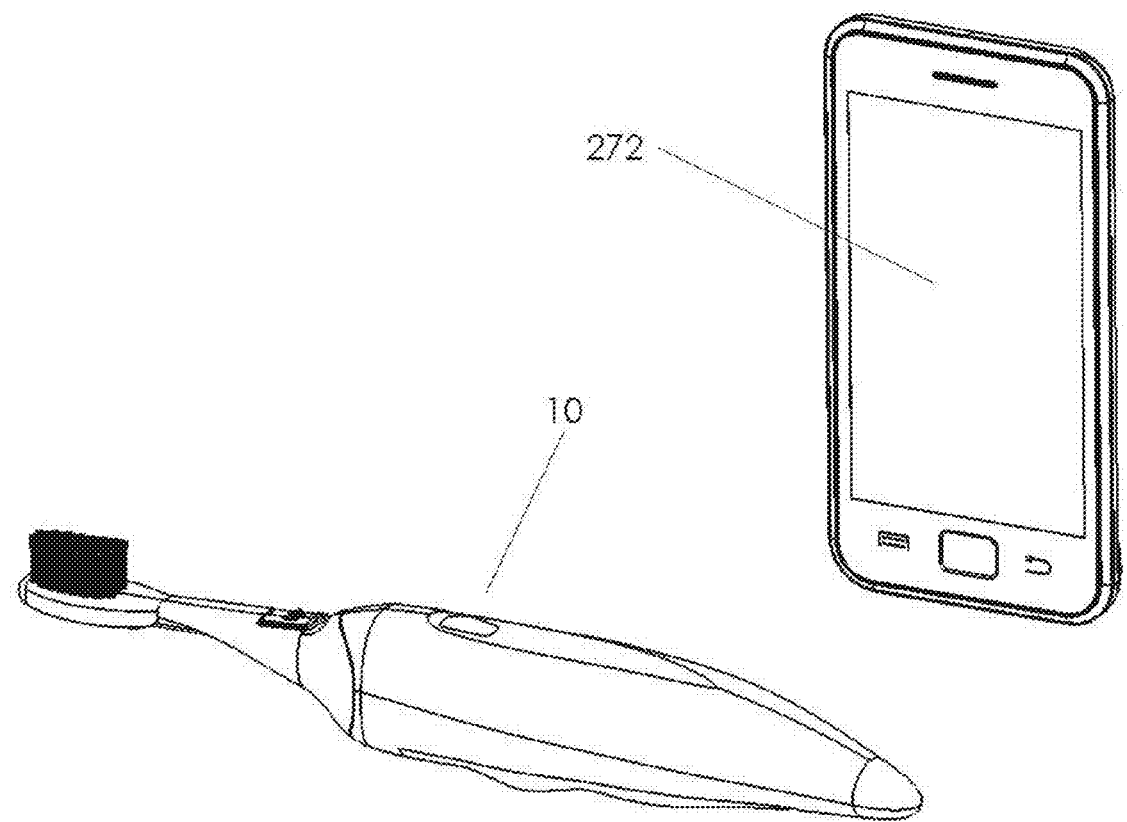
FIG. 10 is a perspective view of a toothbrush and a mobile communication device according to multiple embodiments and alternatives.
Figure 11:
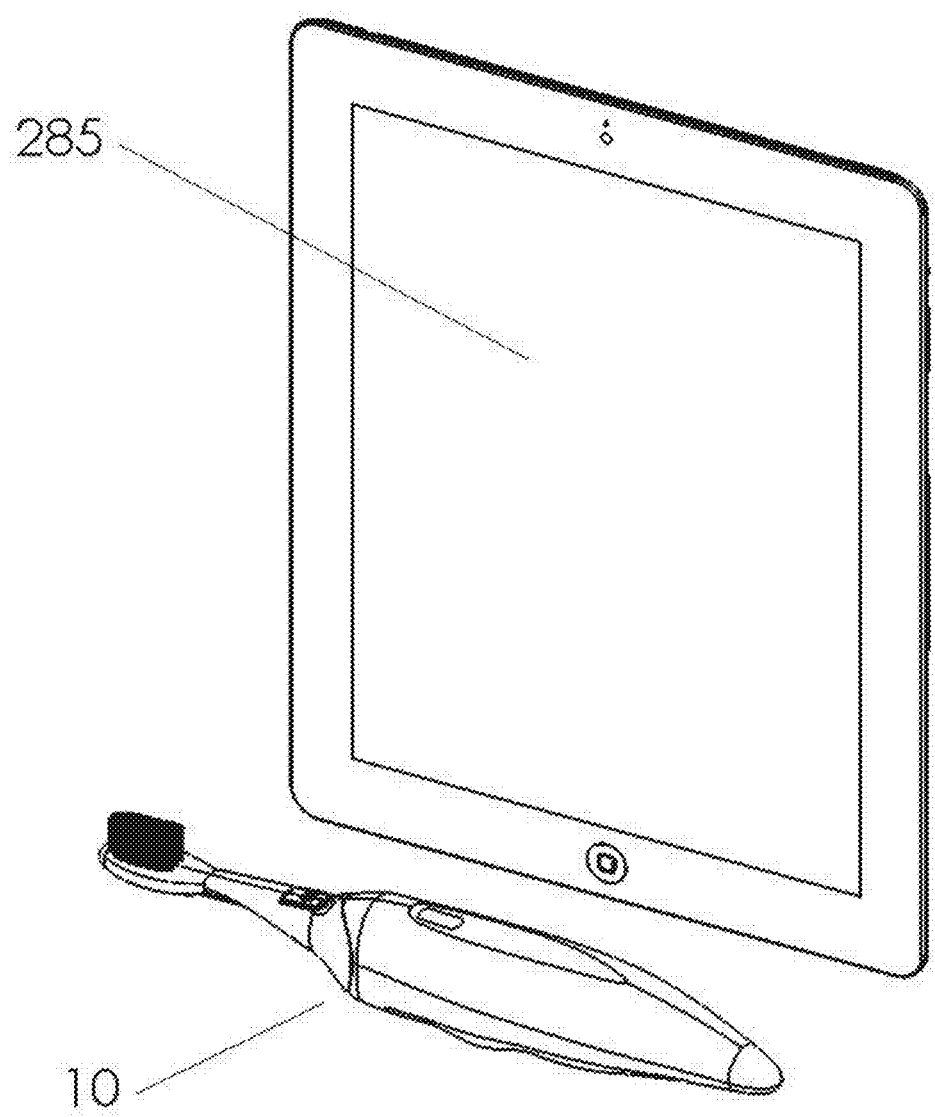
FIG. 11 is a perspective view of a toothbrush and a tablet personal computer according to multiple embodiments and alternatives.
Figure 12:
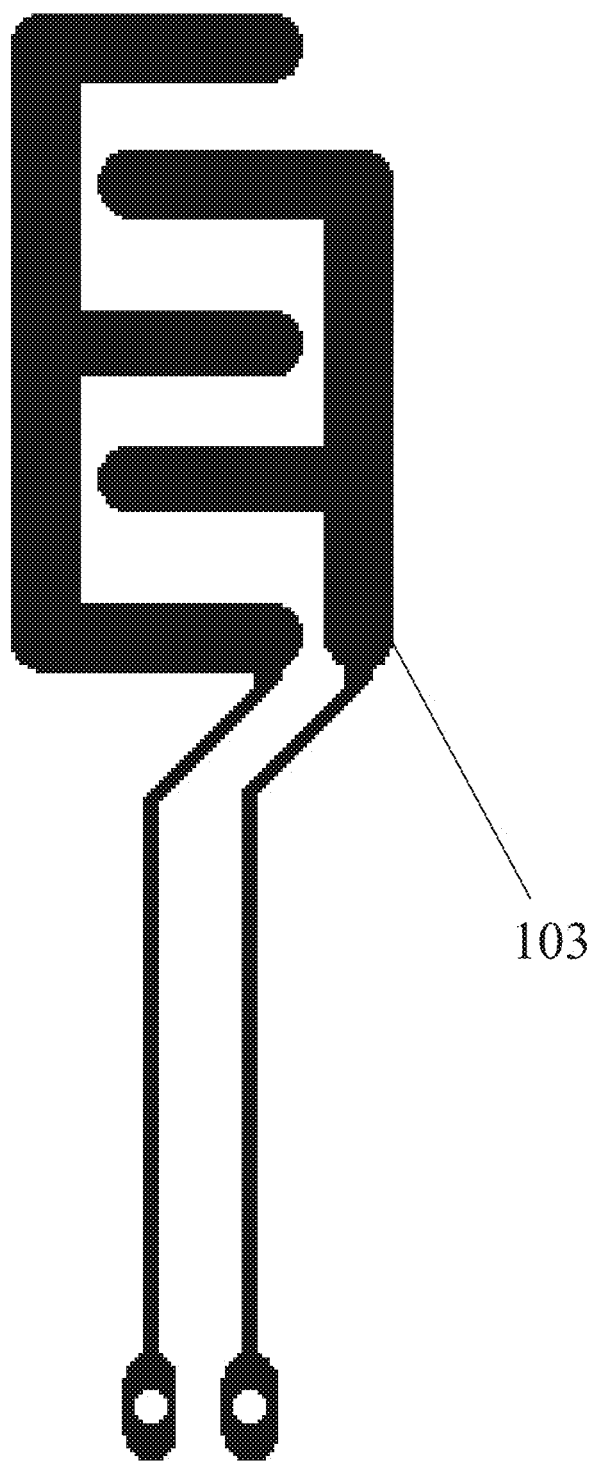
FIG. 12 is a schematic view of a sensor surface of a proximity sensor according to multiple embodiments and alternatives.

The oral health care implement and system with proximity sensor is encompassed in a plurality of preferred embodiments that shall be discussed in the present section.

A plurality of embodiments comprise an oral health care implement. In some embodiments, the oral health care implement is operated in the oral cavity of a human being characterized as the first portion of the alimentary canal that receives food and saliva, and containing a mucous membrane epithelium lining referred to as the oral mucosa. The oral cavity is further characterized as having alveolar arches typically containing teeth, which are either natural, synthetic, or a combination thereof, and used primarily for the preparatory chewing of food for digestion. The implement, in this embodiment, is capable of being operated within the oral cavity, wherein the implement is capable of being operated in a high moisture environment and is manufactured from bio-compatible materials approved for use in the oral cavity.

In some embodiments, the oral health care implement comprises a handle characterized by three general sections, which are a distal end 14, a middle portion, and a proximal end 19. The distal end 14 of the handle is regarded as the end of the handle that is the extreme end away from the user's primary point-of-contact with the handle, which, in some embodiments, is the extreme end away from the user's hand. The distal end 14, in some embodiments, is further characterized as the end of the handle that is most prominently utilized in the implement's working area, which is the oral cavity in a plurality of embodiments. The proximal end 19 of the handle is characterized as the end of the handle that is closest to the user's primary point-of-contact, which, in some embodiments, is the user's point-of-contact with the handle. The middle portion of the handle is characterized as the portion of the handle centrally located between the distal end 14 and the proximal end 19 of the handle.

In some further embodiments, the oral health care implement is a toothbrush 10. A toothbrush 10 is an oral health care implement used for the cleaning of teeth and gingiva, more commonly referred to as gums. A toothbrush 10 comprises a brush head consisting of a plurality of bristles 25 arranged into compact clusters, often referred to as tufts, mounted onto the brush head. Accordingly, the tufts are often mounted in an intentional pattern to facilitate cleaning of teeth and gums. A toothbrush 10 further comprises a handle that includes the brush head and extends proximally from the brush head, which is used for grasping and movement of the toothbrush 10. The handle, consequently, has a distal end 14 and a proximal end 19. The distal end 14 of a toothbrush 10 handle, in some embodiments, is the brush head of the toothbrush 10 where said bristles 25 reside. The proximal end 19 of a toothbrush 10 handle, in some embodiments, is the extreme opposite end from the brush head where the user grasps the handle. In some embodiments, the bristles 25 are manufactured from either a natural material, synthetic material, or a combination thereof. One example of a natural material is animal hair. An example of a typical synthetic material used in toothbrush bristles is Nylon.

In some further embodiments, the oral health care implement is a flosser. A flosser is an oral health care implement used for the removal of food and dental plaque from teeth, especially between teeth and other places a toothbrush cannot effectively clean. A flosser comprises a flosser head having two parallel protrusions with space between them such that a length of dental floss can be placed between the two protrusions. The dental floss is, most often, held taut by the two protrusions to facilitate proper cleaning. A flosser further comprises a handle connected to the flosser head, which may be detachably connected. The handle has a distal end, middle portion, and proximal end such that the middle portion is contained between the distal end and proximal end. Two common orientations exist for the protrusions and the handle including F-shaped wherein the protrusions are generally perpendicular to the long axis of the handle; and the Y-shaped wherein the protrusions are generally parallel to the long axis of the handle. The handle and protrusions are most often manufactured from plastic. The dental floss is typically manufactured from either thin nylon filaments or plastic ribbons. Further variations in dental floss include flavored or unflavored, and waxed or unwaxed.

In other further embodiments, the oral health care implement is a floss pick, which is an oral health care implement used for the removal of food and dental plaque from teeth. The floss pick shares many of the characteristics of the flosser with one major difference at the proximal end of the handle. The proximal end of the handle of the flosser is primarily used for grasping the implement. The proximal end of the floss pick is tapered into a point, much like the end of a toothpick, to further facilitate proper cleaning of teeth. Much like the flosser, the floss pick protrusions also are largely oriented in either an F-shape or Y-shape.

Further still, in some embodiments, the oral health care implement is a gum massager. A gum massager is an oral health care implement used for the stimulation of gums to promote better oral health. A gum massager comprises a massager head shaped to facilitate effective stimulation of gums. The massager head is often in the form of a rubber tip. A gum massager further comprises a handle with a distal end, middle portion, and proximal end. The handle is largely used for movement and manipulation of the implement for proper use.

In some further embodiments, the oral health care implement is a tongue cleaner, which is used for cleaning bacteria, food debris, fungi, and dead cells from the surface of the tongue. A tongue cleaner comprises a cleaning head on the distal end of a handle having a distal end, middle portion, and proximal end. The cleaning head often comprises a plurality of small ridges oriented perpendicular to the long axis of the handle. The ridges are moved along the surface of the tongue to scrap off unwanted matter.

In some embodiments, the oral health care implement is an interdental brush used for cleaning between teeth. An interdental brush comprises a brush head that comprises the small brush sized to fit between a user's teeth. The brush head is located at the distal end of a handle, wherein the handle has a distal end, middle portion, and proximal end. An interdental brush is also commonly referred to as an interproximal brush or a proxy brush.

Alternatively, the oral health care implement is a prophy cup used in dental prophylaxis. A prophy cup is attached to the distal of end of the handle and is often rubber. The prophy cup holds a certain amount of abrasive polishing compound and typically is moved in a rotary motion to facilitate cleaning.

Inherently, an implement has an associated motion when in use which is characterized as either manually driven or electromechanically driven. A manually driven motion is regarded as a motion generated by the user by his/her own power. Conversely, an electromechanically driven motion is characterized as a motion generated by electrical power which is converted to mechanical power used to create the specified electromechanically driven motion. In some embodiments, the electromechanically driven motion is a side-to-side oscillating motion also referred to as a vibratory motion. Often, the vibratory motion is generated by an electric motor with an eccentric weight on the drive shaft of the electric motor. In other instances, the vibratory motion is generated by an electrically conductive coil around the outside of a magnetic mass such that when an alternating current is applied to the coil the magnetic mass oscillates causing vibration of the implement. In some other embodiments, the electromechanically driven motion is a rotation-oscillation motion wherein the brush head rotates either clockwise or counter-clockwise and then rotates in the opposite direction of the first rotation. Electrical power is typically supplied by a battery.

In some embodiments, the oral health care implement comprises a proximity sensor 90. In some embodiments, the proximity sensor 90 is a capacitive sensor. One type of capacitive sensor is a capacitive sensor that works with a frequency change, alternatively referred to as a frequency change capacitive sensor. Optionally, another type of capacitive sensor is a capacitive sensor that works with a capacitive voltage divider, alternatively referred to as a voltage divider capacitive sensor. Both types of capacitive sensors detect the added capacitance of the oral cavity.

In some embodiments, the frequency change capacitive sensor comprises a sensor surface 103, a resistor-capacitor (RC) circuit, and an RC oscillator, wherein the capacitance of the oral cavity introduced by the sensor surface 103 is a parallel capacitance in the RC circuit such that, when the capacitance of the oral cavity is present, the overall capacitance of the RC circuit is altered. The RC oscillator operates at a set frequency controlled by the capacitance of the RC circuit. The sensor surface 103 comes into proximity of the oral cavity, and, consequently, the capacitance of the oral cavity is introduced to the RC circuit by a connection between the sensor surface 103 and the RC circuit such that the capacitance of the oral cavity is a parallel capacitance to the RC circuit. The change in overall capacitance of the RC circuit changes the frequency of the RC oscillator, thus, indicating the oral cavity is in proximity to the sensor surface 103.

In some embodiments, the frequency of the RC oscillator is compared to a reference value to determine if a change in frequency occurs; therefore, the presence of the oral cavity is detected. Accordingly, three alternatives are presented for performing the comparison between the reference value and the frequency of the RC oscillator. One alternative is to define the reference value as a frequency equivalent to the operating frequency of the RC oscillator when the oral cavity is not in proximity to the sensor surface 103. In this instance, the reference value and the frequency of the RC oscillator are both input into a frequency comparator, wherein the frequency comparator evaluates if the values are similar; and thus, indicating one way or the other.

Optionally, the second alternative for comparison of the reference value and the frequency of the RC oscillator comprises a frequency-to-voltage converter, a DC voltage reference value, and a comparator, wherein the frequency of the RC oscillator is input to the frequency-to-voltage converter and a voltage corresponding to the frequency is output. The comparator compares the output voltage of the frequency-to-voltage converter to the DC voltage reference value. The DC voltage reference value is equivalent to the output voltage of the frequency-to-voltage converter when the oral cavity is not in proximity to the sensor surface 103. Accordingly, the comparator outputs a signal consistent with whether the DC voltage reference value is similar to the output of the frequency-to-voltage converter.

Optionally, the third alternative for comparison of the reference value and the frequency of the RC oscillator is to directly measure the frequency of the signal by counting the number of rising or falling edges in a defined time period utilizing a device similar to a microcontroller. In this manner, a baseline operating frequency may be established, and any deviation in frequency beyond a defined threshold will indicate the oral cavity is in proximity to the sensor surface 103.

In some embodiments, the voltage divider capacitive sensor comprises a sensor surface 103, which provides an analog input; a reference voltage; an analog-to-digital converter (A/DC); and a A/DC capacitor. The A/DC is internally driven to the reference voltage such that the A/DC capacitor is fully charged, and the analog input of the sensor surface 103 is internally grounded such that the sensor surface 103 is fully discharged. Next, the analog input of the sensor surface 103 is internally disconnected from the ground and is internally connected to the A/DC such that the A/DC capacitor will discharge at least a portion of its charge to the sensor surface 103 in order to equal the voltages of the sensor surface 103 and the A/DC capacitor. If the oral cavity is in proximity to the sensor surface 103, the sensor will appear to have a larger capacitance. Said larger capacitance results in a many time smaller steady-state voltage between the A/DC capacitor and the sensor as compared to the condition when the sensor is in its normal, low capacitance state. The A/DC may measure the analog input and compare it to a threshold to determine if the sensor surface 103 is in proximity to the oral cavity. The voltage provided to the A/DC will decrease in a manner indicative of the oral cavity's proximity to the sensor surface 103. In some embodiments, the decrease in a manner indicative of the oral cavity's proximity to the sensor surface 103 is significant.

In some embodiments, the reference voltage, the A/DC, and the A/DC capacitor are comprised in a microcontroller such that circuit comprises a sensor surface 103 with an analog input connected to the microcontroller. The A/DC of the microcontroller converts the voltage provided to the A/DC from an analog signal to a digital signal. The microcontroller determines whether the sensor surface 103 is in proximity to the oral cavity based on the digital signal.

In some embodiments, the sensor surface 103 is a conductive material and covered with an insulator material 97 such that the sensor surface 103 can be embedded into the distal end 14 of the handle of the implement. Alternatively, in embodiments where the implement is a toothbrush 10, the sensor surface 103 may be embedded in the brush head or the neck of the toothbrush 10. The sensor surface 103 embedded in the brush head or the neck of the toothbrush 10 would allow for proximity detection of the oral cavity when the toothbrush 10 was used for brushing a user's teeth, thus, providing information for when a toothbrush 10 is in use; or, alternatively, not in use.

In some embodiments, the insulator material 97 covering the sensor surface 103 is the same material as the body of the implement. In some embodiments where the implement is a toothbrush 10, the insulator material 97 covering the sensor surface 103 is the same material as the body of the toothbrush 10 or the outer surface of the brush head.

An issue resides with the presence of water similarly producing a capacitance that may affect the sensor surface 103. A desirable advancement of the present invention is to negate the issue of water unwantedly providing a capacitance indicative of the oral cavity's proximity to the sensor surface 103. In some embodiments, the negation of water is provided by an effective thickness of insulator material 97 separating the water from the sensor surface 103. The insulator material 97 allows detection of the sensor surface 103 in proximity to the oral cavity but does not allow detection of the sensor surface 103 in proximity to water. Alternatively, in some embodiments where the implement is a toothbrush 10, the sensor surface 103 is functionally coupled to the bristles 25 of the brush head such that the bristles act as an insulator material. In the same manner, the bristles 25 allow detection of the sensor surface 103 in proximity to the oral cavity but do not allow detection of the sensor surface 103 in proximity to water.

In some embodiments, the capacitance sensor may be constructed from two parallel conductive plates separated by an insulator such that, in the active portion of the sensor, the insulator allows for an air gap between the parallel plates. For example, the insulator comprises a hole that allows for an air gap between the parallel plates. Forces acting perpendicular to the plane of the parallel plates in the active region deform one conductor or both conductors. Accordingly, the parallel plates move closer together due to deformation, thus, increasing the capacitance of the sensor. In some embodiments where the implement is a toothbrush 10, the bristles 25 comprised in the brush head are operatively attached to at least one of the parallel plates, wherein the act of brushing may be detected by the force exerted by the bristles 25 on the brush head. Thus, the act of brushing indicates the sensor is in proximity to the oral cavity.

In some embodiments, the proximity sensor 90 is a contact microphone, wherein the contact microphone detects vibration. The contact microphone detects vibration created by the use of the implement in the oral cavity. In some embodiments, the contact microphone is in contact with at least a portion of the body of the implement, such that the created vibrations are attenuated by the body of the implement. The vibrations detected by the contact microphone are compared to a reference that correlates to the detection of the implement in the proximity of the oral cavity. If the detected vibrations match the reference value, then the implement is in proximity to the oral cavity.

In some embodiments, the contact microphone is substantially contained in a portion of the implement chosen from the distal end 14, the middle portion, the proximal end 19, and any combination thereof. In some embodiments, the contact microphone is chosen from the group condenser microphone, electret condenser microphone, dynamic microphone, ribbon microphone, carbon microphone, piezoelectric microphone, fiber optic microphone, laser microphone, liquid microphone, microelectromechanical system (MEMS) microphone, and any combination thereof.

Accordingly, a condenser microphone has a diaphragm that acts as one plate of a capacitor and vibrations alter the distance between the plates of the capacitor. Two-types of condenser microphones exist varying in the method of extracting the audio signal. The first type is DC-biased, wherein the plates are biased with a fixed charge and the voltage across the capacitor varies with variance in the capacitance due to vibrations. The second type is radio frequency (RF), wherein a low RF voltage is generated by a low-noise oscillator and the signal from the oscillator is amplitude modulated by the capacitance changes caused by the sound waves moving the capsule diaphragm.

Similarly, an electret condenser microphone is consistent with a condenser microphone with one main difference being that the applied charge is provided by the permanent charge of an electret material. An electret material is a ferroelectric material that is permanently electrically charged or polarized.

Alternatively, a dynamic microphone has a small, movable induction coil that is located in the magnetic field of a permanent magnet, wherein the induction coil is attached to the diaphragm. As the diaphragm vibrates, the induction coil moves about the magnetic field causing a varying current in the coil through electromagnetic induction.

Similarly, a ribbon microphone operates based on magnetic induction. A thin, often corrugated, metal ribbon is suspended in a magnetic field such that the metal ribbon is operably connected to the microphone's output. The vibration of the metal ribbon within the magnetic field generates the electrical signal.

A carbon microphone utilizes a capsule containing carbon granules pressed between two metal plates, one of which is the diaphragm that vibrates in conjunction with sound waves. A voltage is applied across the metal plates that causes current to flow through the carbon granules. As the diaphragm vibrates, varying pressure is applied to the carbon granules, which causes them to deform and vary the contact area between each carbon granule. This variation changes the electrical resistance of the carbon granules, thus changing the current flowing through the microphone and causing the electrical signal.

Alternatively, a piezoelectric microphone utilizes the property of piezoelectricity exhibited by some materials. The vibrations are received by the piezoelectric material which translates the varying vibrations into varying electrical signals. Piezoelectric microphones are the most common type of contact microphone.

A fiber optic microphone operates by passing a laser source through the fiber optic that illuminates a reflective diaphragm. The diaphragm receives sound vibrations, which varies the intensity of the reflected light. The modulated light then passes through a second fiber optic on to a photo detector, which transforms the light into an electrical signal.

A laser microphone utilizes a laser beam aimed at a surface that attenuates vibration. The vibrations of the surface change the reflection angle of the laser beam, which is detected and converted into an electrical signal.

Alternatively, a liquid microphone comprises a metal cup filled with liquid and a diaphragm with a connected needle, such that vibrations cause the diaphragm to move up and down. Consequently, the needle oscillates in the water changing the electrical resistance between the needle and the metal cup.

Lastly, a MEMS microphone utilizes a pressure-sensitive diaphragm etched directly onto a silicon chip. The diaphragm is created by MEMS manufacturing techniques. Most often, MEMS microphones operate in a similar fashion to a condenser microphone.

In some embodiments, the proximity sensor 90 transmits at least one signal indicative of proximity. Optionally, the proximity sensor 90 transmits signals utilizing an electrically conductive wire, wherein the electrical output of the proximity sensor 90 is input to the electrically conductive wire and transmitted thereon. The electrical output of the proximity sensor 90 is, otherwise, referred to as the signal indicative of proximity. The electrically conductive wire allows for the transmission of the signal indicative of condition.

In some embodiments, the oral health care implement further comprises a data processing unit 31 having at least one collector, a storage medium, and at least one processor, wherein the collector, storage medium, and processor, respectively, collect, store, and process data indicative of proximity. Accordingly, in some embodiments, the data processing unit is chosen from the group microprocessor, microcontroller, field programmable gate array (FPGA), digital signal processing unit (DSP), application specific integrated circuit (ASIC), programmable logic, and combinations thereof.

Additionally, in some embodiments, the collector of the data processing unit 31 is an electrically conductive wire, wherein the electrically conductive wire receives the electrical output of the proximity sensor 90, such that the electrical output of the proximity sensor 90 is at least one signal indicative of proximity.

Moreover, in some embodiments, the storage medium of the data processing unit 31 is comprised of volatile memory and non-volatile memory, wherein volatile memory is used for short-term storage and processing, and non-volatile memory is used for long-term storage. Accordingly, in some embodiments, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, in some embodiments, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

Further still, in some embodiments, the processor of the data processing unit 31 is chosen from the group microprocessor and microcontroller.

Optionally, in some embodiments, the oral health care implement further comprises at least one data extractor of data indicative of proximity in the form of a signal, such that the data can be extracted to be used by another medium. The signal can be extracted from the oral health care implement via the data extractor, optionally, after being received by the collector, the storage medium, or the processor, all of the data processing unit. Optionally, the data extractor is chosen from the group universal serial bus (USB), serial port, wired Ethernet port, radio frequency, microwave communication, infrared short-range communication, near field communication, and short-range wireless communication via short-wavelength ultra-high frequency radio waves also known as the registered trademark Bluetooth®.

In some embodiments, the oral health care implement comprises a power source 36 that distributes electrical energy to the electrically powered components of the oral health care implement including: the proximity sensor 103, the data processing unit 31, and other components defined as requiring electrical power. Optionally, in some embodiments, the power source 36 is a battery that is comprised of one or more electrochemical cells that convert stored chemical energy into electrical energy, which is then distributed to the remaining electrically powered components. Two primary types of batteries are utilized in some embodiments including disposable batteries and rechargeable batteries. Both types of batteries come in various sizes and types.

Optionally, the power source of the oral health care implement is a cable that temporarily connects the implement to electrical energy, thus delivering electrical energy to the electrically powered components of the implement. In some embodiments, the electrical energy transferred through the cable is chosen from the group alternating current (AC) and direct current (DC).

In some embodiments, the proximity sensor 90 and the data processing unit 31 operate in conjunction to determine and store the usage instances and the usage time of the implement. Thus, the combination of the proximity sensor 90 and the data processing unit 31 provide a usage monitor for the implement.

In some embodiments, the oral health care implement further comprises at least one pressure sensor to determine if the pressure exerted on the implement is excessive in relation to its intended use. In some embodiments, the pressure sensor may be constructed from two parallel conductive plates separated by an insulator such that, in the active portion of the sensor, the insulator allows for an air gap between the parallel plates, referred to as a parallel plate capacitive sensor. For example, the insulator comprises a hole that allows for an air gap between the parallel plates. Forces acting perpendicular to the plane of the parallel plates in the active region deform one conductor or both conductors. Accordingly, the parallel plates move closer together due to deformation, thus, increasing the capacitance of the sensor.

One type of pressure sensor is a parallel plate capacitive sensor that works with a frequency change, alternatively referred to as a frequency change parallel plate capacitive sensor. Optionally, another type of pressure sensor is a parallel plate capacitive sensor that works with a capacitive voltage divider, alternatively referred to as a voltage divider parallel plate capacitive sensor. Both types of pressure sensors detect the added capacitance of the applied pressure of the oral cavity.

In some embodiments, the frequency change parallel plate capacitive sensor comprises at least two conductive sensor surfaces, an intermediary insulator, a resistor-capacitor (RC) circuit, and an RC oscillator, wherein the capacitance of the applied pressure introduced by the sensor surfaces is a parallel capacitance in the RC circuit such that, when the capacitance of the applied pressure is present, the overall capacitance of the RC circuit is altered. The RC oscillator operates at a set frequency controlled by the capacitance of the RC circuit. The sensor surfaces deform due to applied pressure, and, consequently, the capacitance of the deformation due to applied pressure is introduced to the RC circuit by a connection between the sensor surfaces and the RC circuit such that the capacitance of the applied pressure is a parallel capacitance to the RC circuit. The change in overall capacitance of the RC circuit changes the frequency of the RC oscillator, thus, indicating deformation due to applied pressure to the sensor surfaces.

In some embodiments, the frequency of the RC oscillator is compared to a reference value to determine if a change in frequency occurs; therefore, deformation due to applied pressure is detected. Accordingly, three alternatives are presented for performing the comparison between the reference value and the frequency of the RC oscillator. One alternative is to define the reference value as a frequency equivalent to the operating frequency of the RC oscillator when the applied pressure is not excessive. In this instance, the reference value and the frequency of the RC oscillator are both input into a frequency comparator, wherein the frequency comparator evaluates if the values are similar; and thus, indicating one way or the other.

Optionally, the second alternative for comparison of the reference value and the frequency of the RC oscillator comprises a frequency-to-voltage converter, a DC voltage reference value, and a comparator, wherein the frequency of the RC oscillator is input to the frequency-to-voltage converter and a voltage corresponding to the frequency is output. The comparator compares the output voltage of the frequency-to-voltage converter to the DC voltage reference value. The DC voltage reference value is equivalent to the output voltage of the frequency-to-voltage converter when the applied pressure is not excessive. Accordingly, the comparator outputs a signal consistent with whether the DC voltage reference value is similar to the output of the frequency-to-voltage converter.

Optionally, the third alternative for comparison of the reference value and the frequency of the RC oscillator is to directly measure the frequency of the signal by counting the number of rising or falling edges in a defined time period utilizing a device similar to a microcontroller. In this manner, a baseline operating frequency may be established, and any deviation in frequency beyond a defined threshold will indicate the applied pressure is excessive.

In some embodiments, the voltage divider parallel plate capacitive sensor comprises at least two conductive sensor surfaces, which provides an analog input; an intermediary insulator; a reference voltage; an analog-to-digital converter (A/DC); and a A/DC capacitor. The A/DC is internally driven to the reference voltage such that the A/DC capacitor is fully charged, and the analog input of the conductive sensor surfaces is internally grounded such that the sensor surfaces are fully discharged. Next, the analog input of the sensor surfaces is internally disconnected from the ground and is internally connected to the A/DC such that the A/DC capacitor will discharge at least a portion of its charge to the sensor surfaces in order to equal the voltages of the sensor surfaces and the A/DC capacitor. If the applied pressure causing deformation is excessive, the sensor will appear to have a larger capacitance. Said larger capacitance results in a many time smaller steady-state voltage between the A/DC capacitor and the sensor as compared to the condition when the sensor is in its normal, low capacitance state. The A/DC may measure the analog input and compare it to a threshold to determine if the sensor surfaces are excessively deformed due to applied pressure. The voltage provided to the A/DC will decrease in a manner indicative of the deformation due to excessive applied pressure to the sensor surface. In some embodiments, the decrease in a manner indicative of the deformation due to excessive applied pressure is significant.

In some embodiments, the reference voltage, the A/DC, and the A/DC capacitor are comprised in a microcontroller such that circuit comprises at least two conductive sensor surfaces with an analog input and an intermediary insulator connected to the microcontroller. The A/DC of the microcontroller converts the voltage provided to the A/DC from an analog signal to a digital signal. The microcontroller determines whether the applied pressure is excessive based on the digital signal.

In some embodiments where the implement is a toothbrush 10, the bristles 25 comprised in the brush head are operatively attached to at least one of the parallel plates, wherein applied pressure may be detected by the force exerted by the bristles 25 on the brush head.

In some embodiments, the oral health care implement further comprises at least one temperature sensor 120 having a detector and a transmitter. The temperature sensor 120 is chosen from the group thermocouple, thermistor, resistance temperature detector (RTD), infrared temperature sensor, thermopile, thermostat, and silicon bandgap temperature sensor.

In some embodiments, the transmitter of the temperature sensor 120 is an electrically conductive wire, wherein the electrical output of the detector is input to the electrically conductive wire and transmitted thereon. The electrical output of the detector is, otherwise, referred to as the signal indicative of the temperature captured by the detector of the temperature sensor 120. The electrically conductive wire allows for the transmission of the signal indicative of the temperature.

In some embodiments, the detector of the temperature sensor 120 is at least one thermocouple, wherein the thermocouple comprises two different conductors, typically metal alloys, that produce a voltage proportional to a temperature difference between either end of the pair of conductors. Optionally, in some embodiments, the detector of the temperature sensor 120 is at least one thermistor, wherein the thermistor is a resistor that has a certain resistance, which varies significantly with temperature. Thermistors are generally comprised of a ceramic or polymer material.

Optionally, in some embodiments, the detector of the temperature sensor 120 is at least one resistance temperature detector (RTD), wherein the RTD exploits a predictable change in electrical resistance that is dependent upon a change in temperature. In some embodiments, the material of the RTD is platinum. Optionally, in some embodiments, the detector of the temperature sensor 120 is at least one infrared temperature sensor, wherein the temperature of an object is determined by a portion of thermal radiation referred to as blackbody radiation emitted by the object, such that knowing the infrared energy emitted and the object's emissivity allows for the determination of the object's temperature.

Optionally, in some embodiments, the detector of the temperature sensor 120 is at least one thermopile, wherein the thermopile converts thermal energy into electrical energy and is comprised of one or more thermocouples connected in series or parallel. Optionally, in some embodiments, the detector of the temperature sensor 120 is at least one thermostat, wherein the thermostat comprises two different metals that are bonded together to form a bi-metallic strip, such that the difference in linear expansion rates causes a mechanical bending movement when heat is applied. Optionally, in some embodiments, the detector of the temperature sensor 120 is at least one silicon bandgap temperature sensor, wherein the forward voltage of a silicon diode is dependent on temperature, and the temperature is determined by comparing bandgap voltages at two different currents.

In some embodiments, the temperature sensor 120 and the data processing unit 31, both of the implement, operate in conjunction to provide data indicative of user core body temperature, wherein user core body temperature is a user's operating temperature, which can be indicative of problems experienced by the user. The detector of the temperature sensor 120 detects the temperature within the oral cavity and the transmitter transmits a signal indicative of temperature. The collector of the data processing unit 31 receives the signal indicative of temperature, and the storage medium of the data processing unit 31 stores the signal indicative of temperature in the form of data indicative of temperature. The processor of the data processing unit 31 processes the stored data indicative of temperature into data indicative of user core body temperature, and the storage medium of the data processing unit stores the data indicative of user core body temperature.

In some embodiments, the oral health care implement further comprises a pH sensor having a detector and a transmitter. The detector of the pH sensor comprises a reference electrode, which does not change potential with changes in hydrogen ion concentration, and a measuring electrode, which completes the circuit with the test solution, such that the measuring electrode detects changes in the concentration of hydrogen ions. The detector further comprises a preamplifier that converts high-impedance pH electrode signals into low-impedance pH electrode signals that can be accepted by the transmitter.

In some embodiments, the transmitter of the pH sensor is an electrically conductive wire, wherein the electrical output of the detector is input to the electrically conductive wire and transmitted thereon. The electrical output of the detector is, otherwise, referred to as the signal indicative of the pH value captured by the detector of the pH sensor. The electrically conductive wire allows for the transmission of the signal indicative of the pH value.

In some embodiments, pH value is a measure of the acidity or basicity of an aqueous solution, wherein pure water is neutral. A pH value is a number within the limits of the pH scale, which has a range of 0 to 14. Pure water has a pH value of 7, which is the center of the pH scale. A solution with a pH value less than 7 is acidic, and a solution with a pH value greater than 7 is basic or alkaline.

In some embodiments, the pH value of oral fluid is of interest such that certain pH values can be indicative of certain conditions and disease states. Accordingly, in some embodiments, oral fluid is characterized as a combination of saliva and oral mucosal transudate. Saliva is a fluid secreted from the salivary glands of a human and is comprised of mostly water and smaller amounts of electrolytes, mucus, antibacterial compounds, and various enzymes. Oral mucosal transudate is fluid created from the passive transport of serum components through the oral mucosa into the mouth. In some embodiments, oral fluid is a useful source for diagnostic testing.

In some embodiments, the oral health care implement further comprises at least one microfluidic channel, wherein said microfluidic channel collects oral fluid. A microfluidic channel is characterized as having at least one solid side configured to create a depression in a solid surface such that the microfluidic channel can retain collected fluid; the collected fluid is oral fluid, in some embodiments. The microfluidic channel is further characterized as handling small fluid volumes including volumes less than Pico liters. In operation, the microfluidic channel is placed in contact with a targeted fluid, such as oral fluid, which is drawn into the microfluidic channel by the process of capillary action. Advantageously, the microfluidic channel provides faster analysis and response times due to shorter diffusion distances, fast heating, and high surface-to-volume ratios.

Additionally, in some embodiments, the microfluidic channel of the implement collects oral fluid and delivers oral fluid to the detector of the pH sensor. The oral fluid is collected by the microfluidic channel and is placed in contact with the detector of the pH sensor. The detector of the pH sensor detects the pH value of the oral fluid, and the transmitter of the pH sensor transmits a signal indicative of the pH value.

Further, in some embodiments, the oral health care implement comprises a diagnostic ultrasonic sensor 50 having a detector and a transmitter. In some embodiments, the detector of the diagnostic ultrasonic sensor 50 includes at least one ultrasonic transducer and at least one ultrasonic detector. The ultrasonic transducer converts energy into ultrasound and emits said ultrasound, which is sound waves above the normal audible range of human hearing, typically with a frequency of 20 MHz or greater. In some embodiments, the ultrasonic transducer is a piezoelectric transducer which converts electrical energy into ultrasound by applying an alternating current (AC) across piezoelectric material, which holds the property of changing size when a voltage is applied to it. The application of alternating current to piezoelectric material provides a high frequency oscillation of the piezoelectric material. Consequently, very high frequency sound waves, ultrasound, are produced by the high frequency oscillation of the piezoelectric material.

Additionally, in some embodiments, the ultrasonic detector is a piezoelectric detector that receives ultrasonic waves causing the piezoelectric material to oscillate at a high frequency, thus producing an electrical voltage indicative of the frequency of the ultrasonic waves. In some embodiments, the piezoelectric transducer and the piezoelectric detector utilize the same body of piezoelectric material. Accordingly, the combined embodiment of the piezoelectric transducer and the piezoelectric detector is a piezoelectric transceiver, which performs the functions of both the piezoelectric transducer and the piezoelectric detector comprised in one singular body of piezoelectric material. Optionally, the piezoelectric transducer and the piezoelectric detector utilize separate bodies of piezoelectric material.

In some embodiments, the piezoelectric material is chosen from the group Quartz, Berlinite ($AlPO_4$), Potassium sodium tartrate, Topaz ($Al_2SiO_4(F, OH)_2$), Gallium orthophosphate ($GaPO_4$), Langasite ($La_3Ga_5SiO_{14}$), Barium titanate ($BaTiO_3$), Lead titanate ($PbTiO_3$), Lead zirconate titanate ($Pb[Zr_xTi_{1-x}]O_3$, $0 \le x \le 1$), Potassium niobate ($KNbO_3$), Lithium niobate ($LiNbO_3$), Lithium tantalite ($LiTaO_3$), Sodium tungstate ($Na_2WO_3$), Sodium potassium niobate (NaKNb), Bismuth ferrite ($BiFeO_3$), Sodium niobate ($NaNbO_3$), and Polyvinylidene fluoride (PVDF).

Optionally, in some embodiments, the ultrasonic transducer is a magnetostrictive transducer comprising a magnetostrictive material, magnetizing coil, and magnetic enclosure, wherein the combination of the three elements completes a magnetic circuit. Magnetostrictive transducers utilize the magnetostrictive property of the magnetostrictive material to convert the magnetic energy of a magnetic field to ultrasound, which is sound waves above the normal audible range of human hearing, typically with a frequency of 20 MHz or greater. The magnetostrictive property is a material property, common to ferromagnetic materials, where the material is divided into uniform magnetic polarization domains, such that when a magnetic field is applied said domains shift and rotate causing the magnetostrictive material to change size at a high frequency, thus generating high frequency sound waves or ultrasound. In a magnetostrictive transducer, the magnetic field, in some embodiments, is provided by the magnetizing coil wrapped around the magnetostrictive material. The magnetic field of the magnetizing coil is produced by the input of electrical energy into the coil.

Additionally, in some embodiments, the ultrasonic detector is a magnetostrictive detector comprising a magnetostrictive material, magnetizing coil, and magnetic enclosure, wherein the combination of the three elements completes a magnetic circuit. In the same manner as the magnetostrictive transducer, the magnetostrictive detector utilizes the magnetostrictive property of the magnetostrictive material to convert ultrasound to magnetic energy, which alters the magnetic field of the magnetizing coil, thus altering the electrical energy output of the magnetostrictive detector.

In some embodiments, the magnetostrictive material is chosen from the group Cobalt, Terfenol-D, and Metglas 2605SC. In some embodiments, the magnetizing coil is manufactured from an electrically conductive material. Additionally, in some embodiments, the magnetostrictive transducer and the magnetostrictive detector utilize the same magnetostrictive material, magnetizing coil, and magnetic enclosure, consequently embodied as a magnetostrictive transceiver. Optionally, the magnetostrictive transducer and the magnetostrictive detector have separate magnetostrictive materials, magnetizing coils, and magnetic enclosures.

Optionally, in some embodiments, the ultrasonic transducer is a capacitive actuator comprising two conductive plates on either side of a dielectric material, wherein electrical energy is passed from one conductive plate through the dielectric material to the second conductive plate. The passing of electrical energy across the conductive plates causes the conductive plates to acquire opposite charges, which further causes an attractive force to exist between the conductive plates. Electrical energy in the form of alternating current provides high frequency oscillation of the capacitive actuator, thus converting electrical energy into ultrasound.

Additionally, in some embodiments, the ultrasonic detector is a capacitive actuator having the same properties as stated above. The process is reversed in the instance of the ultrasonic detector, such that ultrasound is received that affects the oscillation of the capacitive actuator, and the electrical energy passed between the two conductive plates through the dielectric material is altered as a result.

Optionally, in some embodiments, the ultrasonic detector comprises a waveguide, wherein the ultrasonic wave is emitted into the waveguide where the sound wave is propagated onto a surface. Optionally, the waveguide comprises at least one toothbrush bristle such that it is included in the plurality of existing toothbrush bristles 25.

In some embodiments, the transmitter of the diagnostic ultrasonic sensor 50 is an electrically conductive wire, wherein the electrical output of the detector is input to the electrically conductive wire and transmitted thereon. The electrical output of the detector is, otherwise, referred to as the signal indicative of the condition captured by the detector of the diagnostic ultrasonic sensor 50. The electrically conductive wire allows for the transmission of the signal indicative of the condition.

In some embodiments, the detector of the diagnostic ultrasonic sensor 50 detects at least one condition within the oral cavity of a user. The condition detected by the detector of the diagnostic ultrasonic sensor 50 is indicative of at least a portion of the user's oral health. In some embodiments, the condition is chosen from the group biofilm thickness, plaque, gingivitis, and periodontitis.

In some embodiments, the diagnostic ultrasonic sensor 50 is a microelectromechanical system (MEMS). A microelectromechanical system is characterized as a system comprising miniaturized mechanical and electro-mechanical elements that are fabricated using the techniques of microfabrication. A microelectromechanical system is further characterized as comprising miniaturized structures, referred to as microstructures; miniaturized sensors, referred to as microsensors; miniaturized actuators, referred to as microactuators; and microelectronics. Microsensors and microactuators are commonly referred to as microtransducers, which are miniaturized devices that convert energy from one medium to another, such as mechanical to electrical.

In some embodiments, microelectromechanical systems vary in size from about less than one micron—one micron is one thousandth of a millimeter—to about greater than one millimeter. The relatively miniature size of microelectromechanical systems requires the utilization of certain materials better suited for fabrication at the defined scale. In some embodiments, the materials used for fabrication of microelectromechanical systems are chosen from the group silicon, polymers, metals, and ceramics. Additionally, in some embodiments, the metals used for fabrication are chosen from the group gold, nickel, aluminum, copper, chromium, titanium, tungsten, platinum, and silver.

Accordingly, a plurality of fabrication processes exist for the production of microelectromechanical systems including: deposition processes, patterning processes, and etching processes. Further, in some embodiments, deposition processes to fabricate microelectromechanical systems are chosen from the group physical vapor deposition, sputtering, chemical deposition, chemical vapor deposition, low pressure chemical vapor deposition, plasma enhanced chemical vapor deposition, and thermal oxidation. Further still, in some embodiments, patterning processes to fabricate microelectromechanical systems are chosen from the group Lithography, Photolithography, electron beam lithography, ion beam lithography, and x-ray lithography. In some embodiments, etching processes to fabricate microelectromechanical systems are chosen from the group wet etching, isotropic etching, anisotropic etching, hydrofluoric etching, electrochemical etching, vapor etching, and plasma etching.

In some embodiments, the ultrasonic detector receives ultrasonic waves reflected from each contacted surface within the oral cavity. Accordingly, in some embodiments, a contacted surface is characterized as a transition surface between two substantially different mediums such that the transition surface between biofilm on a tooth and enamel of said tooth creates a contacted surface. Additionally, contacted surfaces exist at the transition surfaces between oral fluid and biofilm; biofilm and enamel; enamel and dentin; dentin and pulp; pulp and cementum; and cementum and gums.

In some embodiments, the oral health care implement further comprises an oximetry sensor 151. In some embodiments, the oximetry sensor 151 is a transmissive pulse oximeter. Optionally, the oximetry sensor 151 is a reflective pulse oximeter. Both types of oximetry sensors detect blood oxygen saturation and/or heart rate.

In some embodiments, the transmissive pulse oximeter comprises two distinct sides that are parallel with a space separating the two sides creating a measuring site such that a portion of the human body may be inserted between the two sides. The portion of the human body most often inserted in the measuring site is chosen from the group index finger, middle finger, ring finger, pinky finger, thumb, toe, ear lobe, and nose. Two light-emitting diodes (LED) are at least partially contained on the first parallel side creating an emitter. In some embodiments, the two LEDs produce beams of light at different frequencies, which include the range of about 600-750 nanometers (nm) and the range of about 850-1000 nm such that the frequencies produce red and infrared light, respectively.

Additionally, in some embodiments of the transmissive pulse oximeter, the second parallel side comprises a photo detector positioned to be opposite of the emitter such that the photo detector receives the emitted light that passes through the measuring site. The photo detector determines the amount of red and infrared light received, thus determining the amount of red and infrared light absorbed. Accordingly, the amounts of red and infrared light are transmitted by the transmitter of the transmissive pulse oximeter to the data processing unit 31 of the implement.

Optionally, the data processing unit 31 of the implement calculates the ratio of red light to infrared light after the emitted light passes though the measuring site and is received by the photo detector. The calculated ratio is compared to a data bank that relates the calculated ratio to blood oxygen saturation values. The heart rate is further determined by the amount of light absorption of the volume of arterial blood. As the heart pumps blood, the volume of arterial blood increases thus creating a pulsatile change in light absorption. The heart rate is determined by the frequency of pulsatile changes representing heart beats.

Optionally, in some embodiments, the reflective pulse oximeter comprises one distinct side, referred to as the contact surface, that comprises both the light emitter and the photo detector such that the emitted light travels into the measuring site and is reflected back to the photo detector. The reflective pulse oximeter allows the user to contact only one surface on the implement. Accordingly, the reflective pulse oximeter may be contacted by the user during the normal operation of the implement such as brushing a user's teeth.

Accordingly, in some embodiments, the reflective pulse oximeter transmits the amounts of red and infrared light received by the photo detector via the transmitter to the data processing unit 31. Similarly, the ratio of red light to infrared light is calculated and compared to a data bank to correlate the ratio to a blood oxygen saturation value. Additionally, the heart rate of the user is determined in the same manner as described for the transmissive pulse oximeter.

In some embodiments, at least a portion of the oximetry sensor 151 is located on the proximal end 19 of the handle such that the user contacts the oximetry sensor during normal operation of the implement. Optionally, at least a portion of the oximetry sensor 151 is located on the middle portion of the handle such that the user contacts the oximetry sensor during normal operation of the implement.

In some embodiments of the transmissive pulse oximeter, the first and second parallel sides are located on the exterior of the handle such that a user may contact the transmissive pulse oximeter when the implement is fully assembled. In some embodiments, the two parallel sides are parallel to the exterior surface of the handle. Optionally, the two parallel sides are perpendicular to the exterior surface of the handle.

In some embodiments of the reflective pulse oximeter, the contact surface is positioned to be flush with the portions of the handle surrounding the reflective pulse oximeter such that the handle and the reflective pulse oximeter are comprised in a smooth surface. Optionally, the contact surface is positioned to be raised above the portions of the handle surrounding the reflective pulse oximeter such that the reflective pulse oximeter is noticeably distinct from the portions of the handle surrounding it. Optionally still, the contact surface is positioned to be flush with the portions of the handle surrounding the reflective pulse oximeter, and at least a portion of the handle not directly surrounding the reflective pulse oximeter is raised such that the reflective pulse oximeter is located in at least a partial depression indicating where the user shall place his/her thumb for contact with the contact surface.

In some embodiments, the oximetry sensor 151 may be a plurality of transmissive pulse oximeters. Optionally, in some embodiments, the oximetry sensor 151 may be a plurality of reflective pulse oximeters. Also, in some embodiments, the oximetry sensor 151 may a combination of at least one transmissive pulse oximeter and at least one reflective pulse oximeter.

In some embodiments, the oximetry sensor 151 transmits at least one signal indicative of oximetry. Optionally, the oximetry sensor 151 transmits signals utilizing an electrically conductive wire, wherein the electrical output of the oximetry sensor 151 is input to the electrically conductive wire and transmitted thereon. The electrical output of the oximetry sensor 151 is, otherwise, referred to as the signal indicative of oximetry. The electrically conductive wire allows for the transmission of the signal indicative of oximetry.

Optionally, in some embodiments, the power source 36 of the oral health care implement is a mechanical self-charging power source, wherein the power source is replenished by the mechanical motion of brushing a user's teeth. Accordingly, the mechanical motion of brushing a user's teeth is characterized as optimized cleaning motion commensurate with the recommendations of at least one dental practitioner. In some embodiments, this motion is characterized as short back-and-forth motions performed in rapid succession such that biofilm is removed from the surface of teeth. Optionally, the power source 36 is replenished by the user shaking the implement apart from brushing of a user's teeth.

In some embodiments, the mechanical self-charging power source is at least one induction coil and at least one neodymium magnet, wherein the motion of the implement causes the magnet move along the induction coil, which converts the kinetic energy of the magnet into electrical energy. In some embodiments, the electrical energy created by the induction coil and magnet is stored in a rechargeable battery.

In some embodiments, the oral health care implement is a dedicated device utilized for detecting proximity and transmitting at least one signal to the data processing unit, and no other purpose. A dedicated device comprises only a handle, a proximity sensor contained at least partially within the distal end of the handle, a data processing unit, and a power source, wherein the dedicated device is not used for any secondary purpose; a secondary purpose being brushing teeth. In some embodiments, a dedicated device is marketed to detect proximity with the proximity sensor and transmit at least one signal to the data processing unit.

A plurality of embodiments comprise an oral health care system. In some embodiments, the oral health care system comprises an implement and a first data transfer medium 201. In some embodiments, the implement of the oral health care system is the oral health care implement described in the plurality of embodiments comprising the oral health care implement. Accordingly, the implement of the oral health care system, in some embodiments, comprises a handle, a proximity sensor 90, a data processing unit 31, a transmitter, and a power source 36.

In some embodiments, the first data transfer medium 201 of the oral health care system comprises a receiver and a data processing unit. The data processing unit of the first data transfer medium is consistent with the data processing unit 31 of the oral health care implement. Accordingly, in some embodiments, the data processing unit is chosen from the group microprocessor, microcontroller, field programmable gate array (FPGA), digital signal processing unit (DSP), application specific integrated circuit (ASIC), programmable logic, and combinations thereof.

Additionally, in some embodiments, the collector of the data processing unit is an electrically conductive wire, wherein the electrically conductive wire receives the electrical output of the receiver of the first data transfer medium, such that the electrical output of the receiver of the first data transfer medium is at least one signal indicative of proximity.

Moreover, in some embodiments, the storage medium of the data processing unit is comprised of volatile memory and non-volatile memory, wherein volatile memory is used for short-term storage and processing, and non-volatile memory is used for long-term storage. Accordingly, in some embodiments, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, in some embodiments, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

Further still, in some embodiments, the processor of the data processing unit is chosen from the group microprocessor and microcontroller.

Additionally, in some embodiments, the receiver of the first data transfer medium 201 is chosen from the group universal serial bus (USB), serial port, wired Ethernet port, radio frequency, microwave communication, infrared short-range communication, near field communication, and Bluetooth®. The receiver of the first data transfer medium 201 receives at least one signal indicative of proximity from the data extractor of the oral health care implement.

In some embodiments, a signal indicates data as a measurable quantity relevant to proximity detected by the detector of the proximity sensor and is in a form chosen from the group digital and analog. The signal is further characterized as capable of being transmitted, received, collected, stored, processed, and displayed.

Optionally, in some embodiments, data is characterized as qualitative or quantitative attributes of at least one variable, such as proximity Data is further characterized as able to be encoded into at least one signal for transmitting, receiving, collecting, storing, processing, and displaying of data. Data is capable of being collected, stored, and processed.

In some embodiments, the first data transfer medium 201 is a personal computer system 259, which is any general-purpose computer with a size and capability conducive to direct operation by an end-user. Optionally, the first data transfer medium 201 is a dental office computer system 264, which is any computer primarily used in a dental office for dental care purposes. Optionally, in some embodiments, the first data transfer medium 201 is a tablet personal computer 285, wherein the display medium and user input medium are comprised in a singular flat touch screen, and the tablet personal computer 285 is a complete mobile computing system.

Optionally, in some embodiments, the first data transfer medium 201 is a mobile communication device 272 capable of receiving and transmitting telephone calls. Optionally, in some embodiments, the first data transfer medium 201 is a dedicated system 277 utilized only for the purposes set out for the first data transfer medium 201. Optionally, in some embodiments, the first data transfer medium 201 is a television 253. Additionally, in some embodiments, the first data transfer medium 201 is an external charging station 308 that replenishes the electrical energy of the power source of the implement.

Optionally, in some embodiments, the first data transfer medium 201 is a network router 291 that forwards data packets between telecommunications networks, e.g. between the Internet and a personal computer. Optionally, in some embodiments, the first data transfer medium 201 is a web-enabled network storage device 299 that is connected to the internet and acts as a database, commonly referred to as the "Cloud."

In some embodiments, the first data transfer medium 201 further comprises a transmitter. Optionally, the transmitter of the first data transfer medium 201 is chosen from the group universal serial bus (USB), serial port, wired Ethernet port, radio frequency, microwave communication, infrared short-range communication, near field communication, and Bluetooth®.

In some embodiments, the first data transfer medium 201 further comprises a display, wherein the display converts signals into a user-readable format 401. The user-readable format 401 is characterized as a format that allows a user to easily determine the measurement from the display device. In some embodiments, the user-readable format 401 is Arabic numerals.

In some embodiments, the first data transfer medium 201 further comprises a user interface 427 for product selection and purchase options. The user interface 427, in some embodiments, is embodied in the display such that the user interface 427 can be viewed and manipulated using the display. Optionally, the user interface 427 is manipulated through at least one medium external to the display. Alternatively, the user interface 427 is manipulated using the display and at least one medium external to the display. Additionally, the user interface 427 allows for product selection from an online catalog of products. In some embodiments, the online catalog of products is comprised primarily of dental products. The display shows the products of the online catalog in a form chosen from the group at least one image, at least one description, at least one title, at least one price, at least one product review, and any combination thereof. In some embodiments, the user interface 427 allows for the browsing of a plurality of products contained in the online catalog.

Additionally, in some embodiments, the user interface 427 further comprises display space for advertising of products relevant to the user. In some embodiments, data collected by the implement and transmitted to the first data transfer medium 201 is utilized to determine products relevant to the user, e.g. a user who had a high concentration of biofilm thickness would receive an advertisement for a mouthwash intended to breakdown biofilm.

Further, in some embodiments, the user interface 427 presents purchase options on the display, such that a user can view a product and choose at least one option for purchasing the product. The purchase options perform an action chosen from the group add the product to an online cart, purchase the product directly, direct the user to a separate page to purchase the product, direct to a separate page of price comparisons between retailers, direct to a separate page of physical retailers offering the item, and any combination thereof.

Reiterating, in some embodiments, the user interface 427 presents a plurality of dental products from at least one online catalog on the display of the first data transfer medium 201, wherein the user browses products for product selection and purchases products utilizing the purchasing options.

In some embodiments, the user interface 427 facilitates the user's participation in social games related to the data collected by the sensors of the implement. Participation in said social games is accomplished passively through the collection of data by the sensors of the implement over a period of time, rather than participation by real-time user input. Optionally, the social games consist of goals to be accomplished, competitive games between multiple users or between a singular user and a computer generated user, and challenges to complete specified milestones.

Participation in social games is accomplished through a plurality of different user groups. The first user group for participation is a closed loop user group, which is accomplished on a specific data transfer medium and participation is limited to the users of said specific data transfer medium. The second user group for participation is a networked user group, which is accomplished over a network that connects a plurality of data transfer mediums. Networked user groups are further defined as including users belonging to a certain group defined through social media or other means. The third user group for participation is a global user group, which is a user group that anyone can join and participate in. The global user group, in some embodiments, may be sponsored or promoted by a particular entity as a form of advertisement or incentive to the users of the global user group.

Participation in social games may be incentivized with an offered reward to encourage participation of members of a user group. Rewards may include coupons, discounts on goods or services, virtual currency, insurance discounts, and customized incentives. Rewards have the advantage of being given based off of passive data collected by sensors, thus rewarding users for health compliance and health statistics.

In some embodiments, the oral health care system further comprises a second data transfer medium 211 that comprises a receiver, a transmitter, and a data processing unit. The data processing unit of the second data transfer medium 211 is consistent with the data processing unit 31 of the oral health care implement. Accordingly, in some embodiments, the data processing unit is chosen from the group microprocessor, microcontroller, field programmable gate array (FPGA), digital signal processing unit (DSP), application specific integrated circuit (ASIC), programmable logic, and combinations thereof.

Additionally, in some embodiments, the collector of the data processing unit is an electrically conductive wire, wherein the electrically conductive wire receives the electrical output of the receiver of the second data transfer medium, such that the electrical output of the receiver of the second data transfer medium is at least one signal indicative of proximity.

Moreover, in some embodiments, the storage medium of the data processing unit is comprised of volatile memory and non-volatile memory, wherein volatile memory is used for short-term storage and processing, and non-volatile memory is used for long-term storage. Accordingly, in some embodiments, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, in some embodiments, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

Further still, in some embodiments, the processor of the data processing unit is chosen from the group microprocessor and microcontroller.

Additionally, in some embodiments, the receiver of the second data transfer medium 211 is chosen from the group universal serial bus (USB), serial port, wired Ethernet port, radio frequency, microwave communication, infrared short-range communication, near field communication, and Bluetooth®.

In some embodiments, the second data transfer medium 211 is a personal computer system 259, which is any general-purpose computer with a size and capability conducive to direct operation by an end-user. Optionally, the second data transfer medium 211 is a dental office computer system 264, which is any computer primarily used in a dental office for dental care purposes. Optionally, in some embodiments, the second data transfer medium 211 is a tablet personal computer 285, wherein the display medium and user input medium are comprised in a singular flat touch screen, and the tablet personal computer 285 is a complete mobile computing system.

Optionally, in some embodiments, the second data transfer medium 211 is a mobile communication device 272 capable of receiving and transmitting telephone calls. Optionally, in some embodiments, the second data transfer medium 211 is a dedicated system 277 utilized only for the purposes set out for the second data transfer medium 211. Optionally, in some embodiments, the second data transfer medium 211 is a television 253. Additionally, in some embodiments, the second data transfer medium 211 is an external charging station 308 that replenishes the electrical energy of the power source of the implement.

Optionally, in some embodiments, the second data transfer medium 211 is a network router 291 that forwards data packets between telecommunications networks, e.g. between the Internet and a personal computer. Optionally, in some embodiments, the second data transfer medium 211 is a web-enabled network storage device 299 that is connected to the internet and acts as a database, commonly referred to as the "Cloud."

In some embodiments, the second data transfer medium 211 further comprises a transmitter. Optionally, the transmitter of the second data transfer medium 211 is chosen from the group universal serial bus (USB), serial port, wired Ethernet port, radio frequency, microwave communication, infrared short-range communication, near field communication, and Bluetooth®.

In some embodiments, the second data transfer medium 211 further comprises a display, wherein the display converts signals into a user-readable format 401. The user-readable format 401 is characterized as a format that allows a user to easily determine the measurement from the display device. In some embodiments, the user-readable format 401 is Arabic numerals.

In some embodiments, the second data transfer medium 211 further comprises a user interface 427 for product selection and purchase options. The user interface 427, in some embodiments, is embodied in the display such that the user interface 427 can be viewed and manipulated using the display. Optionally, the user interface 427 is manipulated through at least one medium external to the display. Alternatively, the user interface 427 is manipulated using the display and at least one medium external to the display. Additionally, the user interface 427 allows for product selection from an online catalog of products. In some embodiments, the online catalog of products is comprised primarily of dental products. The display shows the products of the online catalog in a form chosen from the group at least one image, at least one description, at least one title, at least one price, at least one product review, and any combination thereof. In some embodiments, the user interface 427 allows for the browsing of a plurality of products contained in the online catalog.

Additionally, in some embodiments, the user interface 427 further comprises display space for advertising of products relevant to the user. In some embodiments, data collected by the implement and transmitted to the first data transfer medium is utilized to determine products relevant to the user, e.g. a user who had a high concentration of biofilm thickness would receive an advertisement for a mouthwash intended to breakdown biofilm.

Further, in some embodiments, the user interface 427 presents purchase options on the display, such that a user can view a product and choose at least one option for purchasing the product. The purchase options perform an action chosen from the group add the product to an online cart, purchase the product directly, direct the user to a separate page to purchase the product, direct to a separate page of price comparisons between retailers, direct to a separate page of physical retailers offering the item, and any combination thereof.

Reiterating, in some embodiments, the user interface presents a plurality of dental products from at least one online catalog on the display of the second data transfer medium, wherein the user browses products for product selection and purchases products utilizing the purchasing options.

In some embodiments, the user interface 427 facilitates the user's participation in social games related to the data collected by the sensors of the implement. Participation in said social games is accomplished passively through the collection of data by the sensors of the implement over a period of time, rather than participation by real-time user input. Optionally, the social games consist of goals to be accomplished, competitive games between multiple users or between a singular user and a computer generated user, and challenges to complete specified milestones.

Participation in social games is accomplished through a plurality of different user groups. The first user group for participation is a closed loop user group, which is accomplished on a specific data transfer medium and participation is limited to the users of said specific data transfer medium. The second user group for participation is a networked user group, which is accomplished over a network that connects a plurality of data transfer mediums. Networked user groups are further defined as including users belonging to a certain group defined through social media or other means. The third user group for participation is a global user group, which is a user group that anyone can join and participate in. The global user group, in some embodiments, may be sponsored or promoted by a particular entity as a form of advertisement or incentive to the users of the global user group.

Participation in social games may be incentivized with an offered reward to encourage participation of members of a user group. Rewards may include coupons, discounts on goods or services, virtual currency, insurance discounts, and customized incentives. Rewards have the advantage of being given based off of passive data collected by sensors, thus rewarding users for health compliance and health statistics.

In some embodiments, the oral health care system further comprises a network storage device 246, wherein the network storage device receives, stores, processes, and transmits data indicative of proximity. The network storage device 246 is more commonly referred to, in some instances, as a network connected server. Additionally, in some instances, the network storage device 246 is more commonly referred to as a "Cloud" server, wherein the storage space on the server is paid for as a service.

In some embodiments, the network storage device 246 is connected to a network, wherein the network is chosen from the group Internet or intranet such that an intranet is a network managed and accessed by an internal organization and is not accessible to the outside world. The network is utilized by the network storage device 246 for receiving and transmitting data. The mode for receiving and transmitting data through the network is chosen from the group universal serial bus (USB), serial port, wired Ethernet port, radio frequency, microwave communication, infrared short-range communication, near field communication, and Bluetooth®.

Additionally, in some embodiments, the network storage device 246 processes data using at least one microprocessor, at least one microcontroller, or a combination thereof. The storage of data, in some embodiments, is comprised of volatile memory and non-volatile memory, wherein volatile memory is used for short-term storage and processing, and non-volatile memory is used for long-term storage. Accordingly, in some embodiments, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, in some embodiments, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

The network storage device 246, optionally, is a network server primarily used for storing and processing data. Optionally, the network storage device 246 is comprised of more than one network server such that the network servers operate in conjunction to increase the storing and processing capabilities of the network storage device 246. In some embodiments, the network storage device 246 is provided as a service such that it is physically located at a location separate from the user, and the service provided is the storing and processing of data. In such embodiments, the network storage device 246 is sometimes referred to as the "Cloud."

In some embodiments, the oral health care system further comprises a third data transfer medium 221 that comprises a receiver, a transmitter, and a data processing unit. The data processing unit of the third data transfer medium 221 is consistent with the data processing unit 31 of the oral health care implement. Accordingly, in some embodiments, the data processing unit is chosen from the group microprocessor, microcontroller, field programmable gate array (FPGA), digital signal processing unit (DSP), application specific integrated circuit (ASIC), programmable logic, and combinations thereof.

Additionally, in some embodiments, the collector of the data processing unit is an electrically conductive wire, wherein the electrically conductive wire receives the electrical output of the receiver of the third data transfer medium, such that the electrical output of the receiver of the third data transfer medium is at least one signal indicative of proximity.

Moreover, in some embodiments, the storage medium of the data processing unit is comprised of volatile memory and non-volatile memory, wherein volatile memory is used for short-term storage and processing, and non-volatile memory is used for long-term storage. Accordingly, in some embodiments, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, in some embodiments, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

Further still, in some embodiments, the processor of the data processing unit is chosen from the group microprocessor and microcontroller.

Additionally, in some embodiments, the receiver of the third data transfer medium 221 is chosen from the group universal serial bus (USB), serial port, wired Ethernet port, radio frequency, microwave communication, infrared short-range communication, near field communication, and Bluetooth®.

In some embodiments, the third data transfer medium 221 is a personal computer system 259, which is any general-purpose computer with a size and capability conducive to direct operation by an end-user. Optionally, the third data transfer medium 221 is a dental office computer system 264, which is any computer primarily used in a dental office for dental care purposes. Optionally, in some embodiments, the third data transfer medium 221 is a tablet personal computer 285, wherein the display medium and user input medium are comprised in a singular flat touch screen, and the tablet personal computer 285 is a complete mobile computing system.

Optionally, in some embodiments, the third data transfer medium 221 is a mobile communication device 272 capable of receiving and transmitting telephone calls. Optionally, in some embodiments, the third data transfer medium 221 is a dedicated system 277 utilized only for the purposes set out for the third data transfer medium 221. Optionally, in some embodiments, the third data transfer medium 221 is a television 253. Additionally, in some embodiments, the third data transfer medium 221 is an external charging station 308 that replenishes the electrical energy of the power source of the implement.

Optionally, in some embodiments, the third data transfer medium 221 is a network router 291 that forwards data packets between telecommunications networks, e.g. between the Internet and a personal computer. Optionally, in some embodiments, the third data transfer medium 221 is a web-enabled network storage device 299 that is connected to the internet and acts as a database, commonly referred to as the "Cloud."

In some embodiments, the transmitter of the third data transfer medium 221 is chosen from the group universal serial bus (USB), serial port, wired Ethernet port, radio frequency, microwave communication, infrared short-range communication, near field communication, and Bluetooth®.

In some embodiments, the third data transfer medium 221 further comprises a display, wherein the display converts signals into a user-readable format 401. The user-readable format 401 is characterized as a format that allows a user to easily determine the measurement from the display device. In some embodiments, the user-readable format 401 is Arabic numerals.

In some embodiments, the third data transfer medium 221 further comprises a user interface 427 for product selection and purchase options. The user interface 427, in some embodiments, is embodied in the display such that the user interface 427 can be viewed and manipulated using the display. Optionally, the user interface 427 is manipulated through at least one medium external to the display. Alternatively, the user interface 427 is manipulated using the display and at least one medium external to the display. Additionally, the user interface 427 allows for product selection from an online catalog of products. In some embodiments, the online catalog of products is comprised primarily of dental products. The display shows the products of the online catalog in a form chosen from the group at least one image, at least one description, at least one title, at least one price, at least one product review, and any combination thereof. In some embodiments, the user interface 427 allows for the browsing of a plurality of products contained in the online catalog.

Additionally, in some embodiments, the user interface 427 further comprises display space for advertising of products relevant to the user. In some embodiments, data collected by the implement and transmitted to the first data transfer medium is utilized to determine products relevant to the user, e.g. a user who had a high concentration of biofilm thickness would receive an advertisement for a mouthwash intended to breakdown biofilm.

Further, in some embodiments, the user interface 427 presents purchase options on the display, such that a user can view a product and choose at least one option for purchasing the product. The purchase options perform an action chosen from the group add the product to an online cart, purchase the product directly, direct the user to a separate page to purchase the product, direct to a separate page of price comparisons between retailers, direct to a separate page of physical retailers offering the item, and any combination thereof.

Reiterating, in some embodiments, the user interface 427 presents a plurality of dental products from at least one online catalog on the display of the third data transfer medium, wherein the user browses products for product selection and purchases products utilizing the purchasing options.

In some embodiments, the user interface 427 facilitates the user's participation in social games related to the data collected by the sensors of the implement. Participation in said social games is accomplished passively through the collection of data by the sensors of the implement over a period of time, rather than participation by real-time user input. Optionally, the social games consist of goals to be accomplished, competitive games between multiple users or between a singular user and a computer generated user, and challenges to complete specified milestones.

Participation in social games is accomplished through a plurality of different user groups. The first user group for participation is a closed loop user group, which is accomplished on a specific data transfer medium and participation is limited to the users of said specific data transfer medium. The second user group for participation is a networked user group, which is accomplished over a network that connects a plurality of data transfer mediums. Networked user groups are further defined as including users belonging to a certain group defined through social media or other means. The third user group for participation is a global user group, which is a user group that anyone can join and participate in. The global user group, in some embodiments, may be sponsored or promoted by a particular entity as a form of advertisement or incentive to the users of the global user group.

Participation in social games may be incentivized with an offered reward to encourage participation of members of a user group. Rewards may include coupons, discounts on goods or services, virtual currency, insurance discounts, and customized incentives. Rewards have the advantage of being given based off of passive data collected by sensors, thus rewarding users for health compliance and health statistics.

Figure 13:
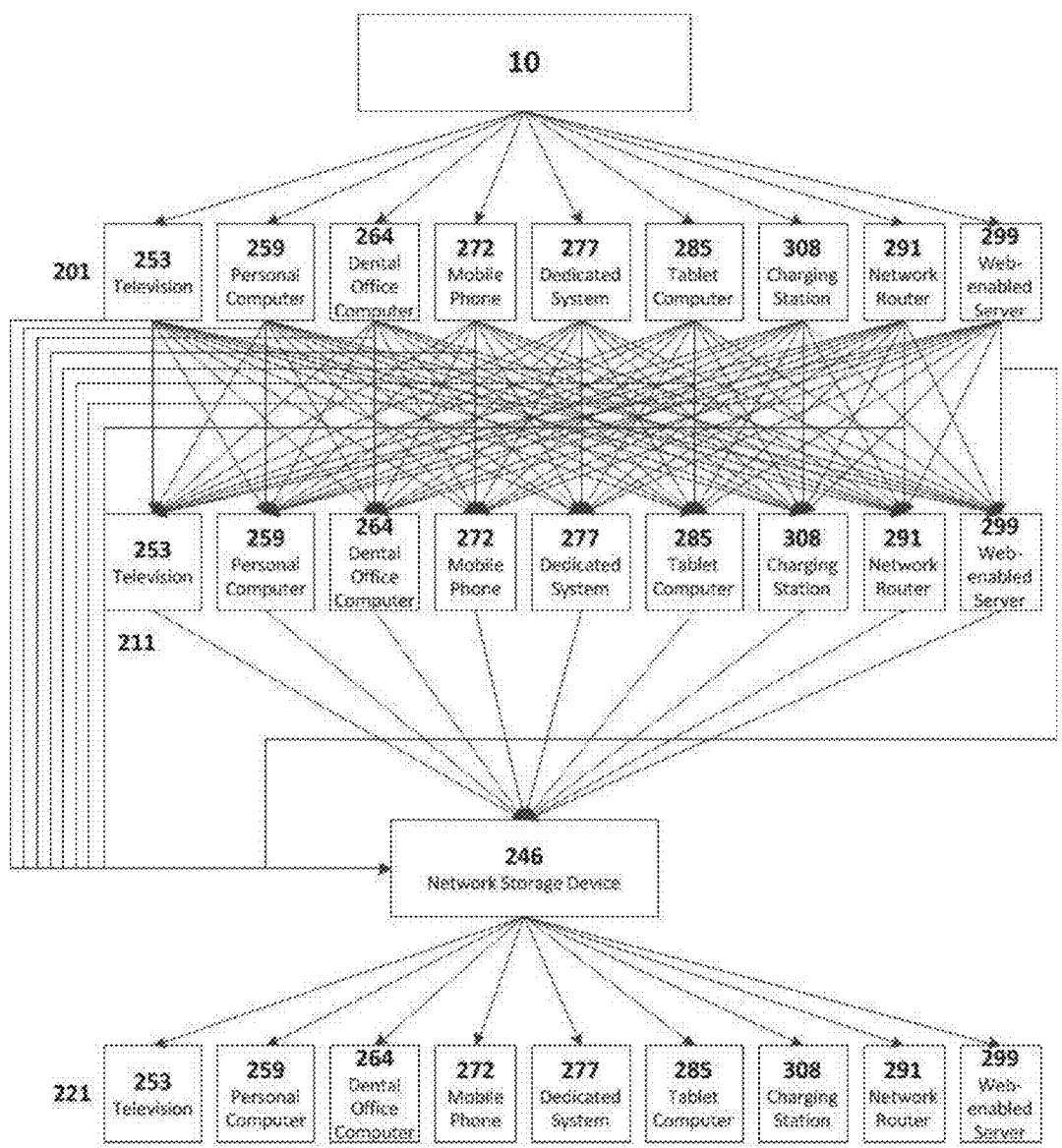
FIG. 13 is a flow diagram of potential data transfer paths according to multiple embodiments and alternatives.
Figure 15:
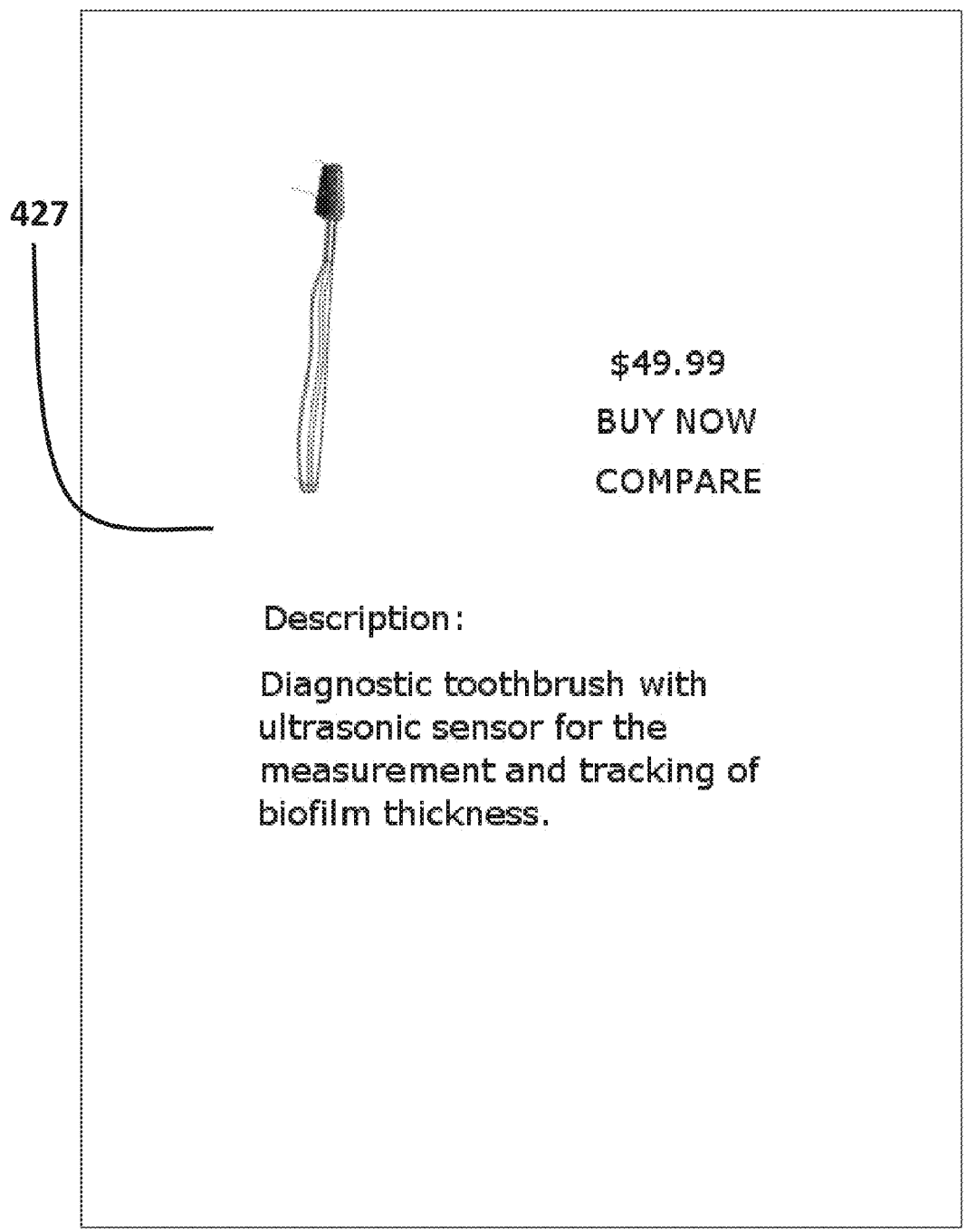
FIG. 15 is an example screen shot of a user interface according to multiple embodiments and alternatives.

Referring to FIG. 13, a plurality of data transfer paths exist in the present embodiments. The data transfer paths are comprised of a combination of the elements of the oral health care system described, wherein the elements are chosen from the group implement, first data transfer medium 201, second data transfer medium 211, network storage device 246, and third data transfer medium 221. Accordingly, the simplest data transfer path is comprised of the implement and the first data transfer medium 201, wherein the implement detects data and transmits data to the first data transfer medium 201, which receives, stores and processes the data. Additionally, the first data transfer medium 201 may display data such that a user can view the data in a user-readable format 401.

Optionally, the above embodiments exemplify data transfer paths of greater complexity. In some embodiments, the data transfer path comprises the implement, the first data transfer medium 201, and the second data transfer medium 211, wherein the implement detects data and transmits data to the first data transfer medium 201, which receives, stores, processes, and transmits the data to the second data transfer medium 211. The second data transfer medium 211 receives, stores, and processes the data. The data is displayed in a user-readable format 401 by the first data transfer medium 201, the second data transfer medium 211, or a combination thereof.

Optionally, in some embodiments, the data transfer path comprises the implement, the first data transfer medium 201, the second data transfer medium 211, and the network storage device 246. The implement detects data and transmits the data to the first data transfer medium 201, and the first data transfer medium 201 receives, stores, processes, and transmits the data. The first data transfer data medium 201 transmits the data to the second data transfer medium 211, wherein the second data transfer medium 211 receives, stores, processes, and transmits the data. The second data transfer medium 211 transmits the data to the network storage device 246. The network storage device 246 receives, stores, and processes the data. The data is displayed in a user-readable 401 format by the first data transfer medium 201, the second data transfer medium 211, or a combination thereof.

Optionally, in some embodiments, the data transfer path comprises the implement, the first data transfer medium 201, the second data transfer medium 211, the network storage device 246, and the third data transfer medium 221. Accordingly, the implement detects data and transmits said data to the first data transfer medium 201. The first data transfer medium 201 receives, stores, processes, and transmits the data, wherein the data is transmitted from the first data transfer medium 201 to the second data transfer medium 211. Additionally, the second data transfer medium 211 receives, stores, processes, and transmits the data. The second data transfer medium 211 transmits the data, and the network storage device 246 receives the data, wherein the network storage device 246 receives, stores, processes, and transmits the data. The third data transfer medium 221 receives the data transmitted by the network storage device 246, and the third data transfer medium 221 receives, stores, processes, transmits, and displays the data. Optionally, the data is displayed by a medium chosen from the group first data transfer medium 201, second data transfer medium 211, third data transfer medium 221, and any combinations thereof. Additionally, data transmitted by the implement, the first data transfer medium 201, the second data transfer medium 211, the network storage device 246, the third data transfer medium 221, or any combination thereof may be received by the first data transfer medium 201, the second data transfer medium 211, the network storage device 246, the third data transfer medium 221, or any combination thereof.

Optionally, in some embodiments, the data transfer path comprises the implement, the first data transfer medium 201, and the network storage device 246. The implement detects data and transmits the data to the first data transfer medium 201. The first data transfer medium 201 receives, stores, processes, and transmits the data. The first data transfer medium 201 transmits the data to the network storage device 246, which receives, stores, processes, and transmits the data. Optionally, the first data transfer medium 201 displays the data in a user-readable format 401.

Optionally, in some embodiments, the data transfer path comprises the implement, the first data transfer medium 201, the network storage device 246, and the third data transfer medium 221. The implement detects data and transmits the data to the first data transfer medium 201, which receives, stores, processes, and transmits the data. The first data transfer medium 201 transmits the data to the network storage device 246, which receives, stores, processes, and transmits the data, where the data is transmits to the third data transfer medium 221. The third data transfer medium 221 receives, stores, processes, transmits, and displays the data. Optionally, the first data transfer medium 201, the third data transfer medium 221, or any combinations thereof display the data in a user-readable format 401.

In some embodiments, the oral health care system further comprises a robotic retrieval system (RRS), wherein the RRS retrieves and packages products ordered from a medium chosen from the group first data transfer medium 201, second data transfer medium 211, third data transfer medium 221, and any combinations thereof. The RRS comprises at least one robotic system that is utilized to retrieve products purchased via the purchase options of the user interface 427. In some embodiments, the user selects a product and purchases the product using the user interface 427 for product selection and purchase options. The purchase is transmitted to the RRS, which then locates the product within a distributor's warehouse and retrieves the product. The retrieved product is brought back to a packaging station where the RRS places the product in a package and prepares the package for shipment. In some embodiments, the user selects more than one product, and the RRS retrieves and packages multiple products in one order for shipment to the user.

It will be understood that the embodiments described herein are not limited in their application to the details of the teachings and descriptions set forth, or as illustrated in the accompanying figures. Rather, it will be understood that an oral health care implement and system with a proximity sensor, as taught and described according to multiple embodiments disclosed herein, is capable of other embodiments and of being practiced or carried out in various ways.

Also, it is to be understood that the phraseology and terminology used herein is for the purpose of description and should not be regarded as limiting. The use herein of "including," "comprising," "e.g.," "containing," or "having," and variations of those words is meant to encompass the items listed thereafter, and equivalents of those, as well as additional items.

Accordingly, the descriptions herein are not intended to be exhaustive, nor are they meant to limit the understanding of the embodiments to the precise forms disclosed. It will be understood by those having ordinary skill in the art that modifications and variations of these embodiments are reasonably possible in light of the above teachings and descriptions.

What is claimed is:

1. An oral health care implement, comprising:
a handle having a distal end, a middle portion, and a proximal end;
a capacitive sensor that is configured to detect if the oral health care implement is in proximity to an oral cavity, the capacitive sensor having a sensor surface that is located on a top side of the distal end and covered by an insulator material;
a data processing unit having a collector, a storage medium, and a processor;
a power source; and
a data extractor;
wherein the capacitive sensor is configured to transmit at least one signal indicative of proximity to the data processing unit.

2. The oral health care implement of claim 1, wherein the oral health care implement is selected from the group consisting of a toothbrush, a flosser, a floss pick, a gum massager, a tongue cleaner, an interdental brush, a prophy cup, a scaler, and a mouth mirror, or any combination thereof.

3. The oral health care implement of claim 2, wherein the distal end of the handle is detachably connected to the remainder of the handle.

4. The oral health care implement of claim 1, further comprising at least one sensor selected from the group consisting of a diagnostic ultrasonic sensor, a temperature sensor, a pressure sensor, a pH sensor, and an oximetry sensor, or any combination thereof.

5. The oral health care implement of claim 1, wherein the data extractor is selected from the group consisting of a universal serial bus, a serial port, a wired Ethernet port, a radio frequency, a microwave communication, an infrared short-range communication, a near field communication, and short-range wireless communication via short-wavelength ultra-high frequency radio waves.

6. The oral health care implement of claim 1, wherein the capacitive sensor is selected from the group consisting of a frequency change capacitive sensor, a voltage divider capacitive sensor, and a capacitive sensor constructed from two parallel conductive plates separated by an insulator.

7. The oral health care implement of claim 1, wherein the oral health care implement is a toothbrush comprising a brush head having a plurality of bristles.

8. The oral health care implement of claim 7, wherein at least a portion of the capacitive sensor is contained within a section of the toothbrush selected from the group consisting of a brush head, a brush neck, and a brush handle, or any combination thereof.

9. The oral health care implement of claim 1, wherein the thickness of the insulator material is conducive to negating the effects of water on the sensor surface.

10. The oral health care implement of claim 1, wherein the oral health care implement is a toothbrush comprising a brush head, and the insulating material comprises a plurality of bristles situated on the top side of the brush head.

11. The oral health care implement of claim 1, wherein the oral health care implement is a toothbrush comprising a brush head, and the insulating material comprises a same material as the handle of the toothbrush.

12. The oral health care implement of claim 1, wherein the power source is a mechanical self-charging power source comprising at least one induction coil and at least one magnet, wherein the motion of the implement causes at least one magnet to move along at least one induction coil.

* * * * *